US010946084B2

(12) United States Patent
Møller et al.

(10) Patent No.: US 10,946,084 B2
(45) Date of Patent: Mar. 16, 2021

(54) **PROTEINS AND NUCLEIC ACIDS USEFUL IN VACCINES TARGETING *STAPHYLOCOCCUS AUREUS***

(71) Applicant: Evaxion Biotech ApS, København K (DK)

(72) Inventors: Niels Iversen Møller, København K (DK); Andreas Holm Mattsson, København K (DK)

(73) Assignee: Evaxion Biotech ApS, Københaven K (DK)

( * ) Notice: Subject to any disclaimer, the term of this patent is extended or adjusted under 35 U.S.C. 154(b) by 0 days.

(21) Appl. No.: 16/078,963

(22) PCT Filed: Feb. 22, 2017

(86) PCT No.: PCT/EP2017/054043
§ 371 (c)(1),
(2) Date: Aug. 22, 2018

(87) PCT Pub. No.: WO2017/144523
PCT Pub. Date: Aug. 31, 2017

(65) Prior Publication Data
US 2019/0046631 A1    Feb. 14, 2019

(30) Foreign Application Priority Data

Feb. 22, 2016  (EP) .................... 16156786

(51) Int. Cl.
*A61K 39/00* (2006.01)
*A61K 39/02* (2006.01)
*A61K 39/085* (2006.01)
*C07K 14/31* (2006.01)
*A61P 31/04* (2006.01)
*A61K 39/39* (2006.01)

(52) U.S. Cl.
CPC ............ *A61K 39/085* (2013.01); *A61K 39/39* (2013.01); *A61P 31/04* (2018.01); *C07K 14/31* (2013.01); *A61K 2039/505* (2013.01); *A61K 2039/55505* (2013.01)

(58) Field of Classification Search
CPC ...... A61K 39/00; A61K 39/02; A61K 39/085; A61K 49/00
USPC ...... 424/9.1, 9.2, 184.1, 185.1, 234.1, 243.1
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,684,611 A | 8/1987 | Schilperoort et al. |
| 4,800,159 A | 1/1989 | Mullis et al. |
| 4,879,236 A | 11/1989 | Smith et al. |
| 4,952,500 A | 8/1990 | Finnerty et al. |
| 5,302,523 A | 4/1994 | Coffee et al. |
| 5,322,783 A | 6/1994 | Tomes et al. |
| 5,384,253 A | 1/1995 | Krzyzek et al. |
| 5,464,765 A | 11/1995 | Coffee et al. |
| 5,538,877 A | 7/1996 | Lundquist et al. |
| 5,538,880 A | 7/1996 | Lundquist et al. |
| 5,550,318 A | 8/1996 | Adams et al. |
| 5,563,055 A | 10/1996 | Townsend et al. |
| 5,580,859 A | 12/1996 | Felgner et al. |
| 5,589,466 A | 12/1996 | Felgner et al. |
| 5,591,616 A | 1/1997 | Hiei et al. |
| 5,610,042 A | 3/1997 | Chang et al. |
| 5,656,610 A | 8/1997 | Shuler et al. |
| 5,702,932 A | 12/1997 | Hoy et al. |
| 5,736,524 A | 4/1998 | Content et al. |
| 5,780,448 A | 7/1998 | Davis |
| 5,789,215 A | 8/1998 | Berns et al. |
| 5,843,650 A | 12/1998 | Segev |
| 5,846,709 A | 12/1998 | Segev |
| 5,846,783 A | 12/1998 | Wu et al. |
| 5,849,497 A | 12/1998 | Steinman |
| 5,849,546 A | 12/1998 | Sousa et al. |
| 5,849,547 A | 12/1998 | Cleuziat et al. |
| 5,858,652 A | 1/1999 | Laffler et al. |
| 5,866,366 A | 2/1999 | Kallender |
| 5,871,986 A | 2/1999 | Boyce |
| 5,916,776 A | 6/1999 | Kumar |
| 5,922,574 A | 7/1999 | Minter |
| 5,925,565 A | 7/1999 | Berlioz et al. |
| 5,928,905 A | 7/1999 | Stemmer et al. |
| 5,928,906 A | 7/1999 | Koster et al. |
| 5,932,451 A | 8/1999 | Wang et al. |
| 5,935,819 A | 8/1999 | Eichner et al. |
| 5,935,825 A | 8/1999 | Nishimura et al. |
| 5,939,291 A | 8/1999 | Loewy et al. |
| 5,942,391 A | 8/1999 | Zhang et al. |
| 5,945,100 A | 8/1999 | Fick |

(Continued)

FOREIGN PATENT DOCUMENTS

| | | |
|---|---|---|
| GB | 2202328 | 9/1988 |
| WO | WO9014837 | 12/1990 |
| WO | WO9409699 | 5/1994 |
| WO | WO2011127032 | 10/2011 |
| WO | WO2012136653 | 10/2012 |
| WO | WO2013040142 | 3/2013 |

(Continued)

OTHER PUBLICATIONS

Kohler, G. et al, "Continuous cultures of fused cells secreting antibody of predefined specificity", Nature, vol. 256, pp. 495-497, (1975).

*Primary Examiner* — Rodney P Swartz

(74) *Attorney, Agent, or Firm* — McHale & Slavin, P.A.

(57) ABSTRACT

The present invention relates to proteins and nucleic acids derived from *Staphylococcus aureus* as well as therapeutic and diagnostic uses of the proteins and nucleic acids.

13 Claims, 3 Drawing Sheets

Figure 1:
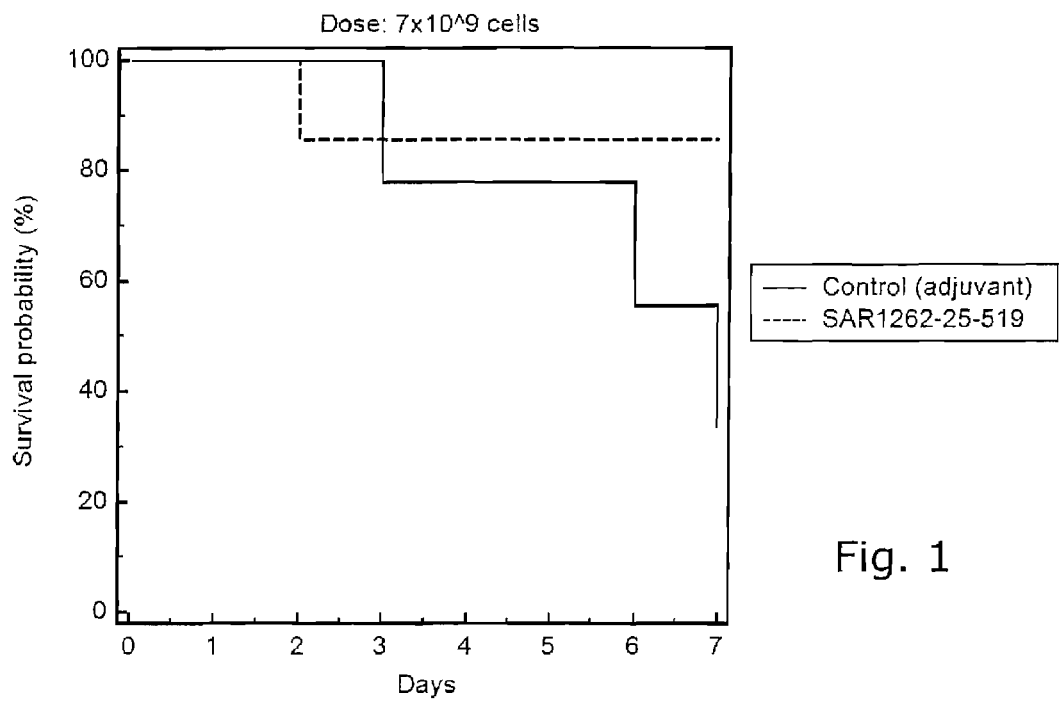

Specification includes a Sequence Listing.

(56) References Cited

U.S. PATENT DOCUMENTS

| | | | |
|---|---|---|---|
| 5,981,274 A | 11/1999 | Tyrrell et al. | |
| 5,994,624 A | 11/1999 | Trolinder et al. | |
| 2006/0073161 A1 | 4/2006 | Breton | |
| 2007/0118916 A1* | 5/2007 | Puzio | C12N 15/8214 800/278 |

FOREIGN PATENT DOCUMENTS

| | | |
|---|---|---|
| WO | WO2013092985 | 6/2013 |
| WO | WO2015053899 | 4/2015 |
| WO | WO2015082536 | 6/2015 |

\* cited by examiner

SEQUENCE LISTING

```
<160> NUMBER OF SEQ ID NOS: 6

<210> SEQ ID NO 1
<211> LENGTH: 199
<212> TYPE: PRT
<213> ORGANISM: Staphylococcus aureus

<400> SEQUENCE: 1

Met Thr Glu Lys Glu Lys Met Leu Ala Glu Lys Trp Tyr Asp Ala Asn
1               5                   10                  15

Phe Asp Gln Asp Leu Ile Asn Glu Arg Ala Arg Ala Lys Asp Ile Cys
            20                  25                  30

Phe Glu Leu Asn His Thr Lys Pro Ser Asp Lys Asn Lys Arg Lys Glu
        35                  40                  45

Leu Ile Asp Glu Leu Phe Gln Thr Thr Thr Asp Asn Val Ser Ile Ser
    50                  55                  60

Ile Pro Phe Asp Thr Asp Tyr Gly Trp Asn Val Lys Leu Gly Lys Asn
65                  70                  75                  80

Val Tyr Val Asn Thr Asn Cys Tyr Phe Met Asp Gly Gly Gln Ile Thr
                85                  90                  95

Ile Gly Asp Asn Val Phe Ile Gly Pro Asn Cys Gly Phe Tyr Thr Ala
            100                 105                 110

Thr His Pro Leu Asn Phe His His Arg Asn Glu Gly Phe Glu Lys Ala
        115                 120                 125

Gly Pro Ile Asn Ile Gly Ser Asn Thr Trp Phe Gly Gly His Val Ala
    130                 135                 140
```

```
Val Leu Pro Gly Val Thr Ile Gly Glu Gly Ser Val Ile Gly Ala Gly
145                 150                 155                 160

Ser Val Val Thr Lys Asp Ile Pro Pro His Ser Leu Ala Val Gly Asn
                165                 170                 175

Pro Cys Lys Val Val Arg Lys Ile Asp Asn Glu Val Pro Ser Glu Ala
            180                 185                 190

Leu Asn Asp Glu Thr Leu Asn
        195
```

<210> SEQ ID NO 2
<211> LENGTH: 519
<212> TYPE: PRT
<213> ORGANISM: Staphylococcus aureus

<400> SEQUENCE: 2

```
Met Asn Leu Leu Ser Leu Leu Ile Leu Leu Gly Ile Ile Leu Gly
1               5                   10                  15

Val Val Gly Gly Tyr Val Val Ala Arg Asn Leu Leu Gln Lys Gln
                20                  25                  30

Ser Gln Ala Arg Gln Thr Ala Glu Asp Ile Val Asn Gln Ala His Lys
            35                  40                  45

Glu Ala Asp Asn Ile Lys Lys Glu Lys Leu Leu Glu Ala Lys Glu Glu
        50                  55                  60

Asn Gln Ile Leu Arg Glu Gln Thr Glu Ala Glu Leu Arg Glu Arg Arg
65                  70                  75                  80

Ser Glu Leu Gln Arg Gln Glu Thr Arg Leu Leu Gln Lys Glu Asn
                85                  90                  95

Leu Glu Arg Lys Ser Asp Leu Leu Asp Lys Asp Glu Ile Leu Glu
                100                 105                 110

Gln Lys Glu Ser Lys Ile Glu Glu Lys Gln Gln Gln Val Asp Ala Lys
            115                 120                 125

Glu Ser Ser Val Gln Thr Leu Ile Met Lys His Glu Gln Glu Leu Glu
        130                 135                 140

Arg Ile Ser Gly Leu Thr Gln Glu Glu Ala Ile Asn Glu Gln Leu Gln
145                 150                 155                 160

Arg Val Glu Glu Glu Leu Ser Gln Asp Ile Ala Val Leu Val Lys Glu
                165                 170                 175

Lys Glu Lys Glu Ala Lys Glu Lys Val Asp Lys Thr Ala Lys Glu Leu
            180                 185                 190

Leu Ala Thr Ala Val Gln Arg Leu Ala Ala Asp His Thr Ser Glu Ser
        195                 200                 205

Thr Val Ser Val Val Asn Leu Pro Asn Asp Glu Met Lys Gly Arg Ile
210                 215                 220

Ile Gly Arg Glu Gly Arg Asn Ile Arg Thr Leu Glu Thr Leu Thr Gly
225                 230                 235                 240

Ile Asp Leu Ile Ile Asp Asp Thr Pro Glu Ala Val Ile Leu Ser Gly
                245                 250                 255

Phe Asp Pro Ile Arg Arg Glu Ile Ala Arg Thr Ala Leu Val Asn Leu
            260                 265                 270

Val Ser Asp Gly Arg Ile His Pro Gly Arg Ile Glu Asp Met Val Glu
        275                 280                 285

Lys Ala Arg Lys Glu Val Asp Asp Ile Ile Arg Glu Ala Gly Glu Gln
    290                 295                 300

Ala Thr Phe Glu Val Asn Ala His Asn Met His Pro Asp Leu Val Lys
```

```
              305                 310                 315                 320
Ile Val Gly Arg Leu Asn Tyr Arg Thr Ser Tyr Gly Gln Asn Val Leu
                325                 330                 335
Lys His Ser Ile Glu Val Ala His Leu Ala Ser Met Leu Ala Ala Glu
                340                 345                 350
Leu Gly Glu Asp Glu Thr Leu Ala Lys Arg Ala Gly Leu Leu His Asp
                355                 360                 365
Val Gly Lys Ala Ile Asp His Glu Val Glu Gly Ser His Val Glu Ile
            370                 375                 380
Gly Val Glu Leu Ala Lys Lys Tyr Gly Glu Asn Glu Thr Val Ile Asn
385                 390                 395                 400
Ala Ile His Ser His His Gly Asp Val Glu Pro Thr Ser Ile Ile Ser
                405                 410                 415
Ile Leu Val Ala Ala Asp Ala Leu Ser Ala Ala Arg Pro Gly Ala
                420                 425                 430
Arg Lys Glu Thr Leu Glu Asn Tyr Ile Arg Arg Leu Glu Arg Leu Glu
                435                 440                 445
Thr Leu Ser Glu Ser Tyr Asp Gly Val Glu Lys Ala Phe Ala Ile Gln
                450                 455                 460
Ala Gly Arg Glu Ile Arg Val Ile Val Ser Pro Glu Glu Ile Asp Asp
465                 470                 475                 480
Leu Lys Ser Tyr Arg Leu Ala Arg Asp Ile Lys Asn Gln Ile Glu Asp
                485                 490                 495
Glu Leu Gln Tyr Pro Gly His Ile Lys Val Thr Val Val Arg Glu Thr
                500                 505                 510
Arg Ala Val Glu Tyr Ala Lys
            515

<210> SEQ ID NO 3
<211> LENGTH: 600
<212> TYPE: DNA
<213> ORGANISM: Staphylococcus aureus

<400> SEQUENCE: 3
atgactgaaa aagaaaaaat gttagcagaa aaatggtacg atgcaaactt tgatcaagac    60
ttaatcaatg aacgtgcacg agcgaaagat atttgctttg aattaaatca tacaaagccg   120
agtgacaaaa ataaaagaaa ggaattaatc gatgaattat ttcaaacaac aacagacaat   180
gtaagtattt cgattccttt tgatacagat tatggttgga acgttaaact aggaaaaaat   240
gtctatgtaa acaccaattg ttattttatg gatggtggac agattacaat tggcgataat   300 gttttatag gacctaattg tggattctac acagcaacac atccacttaa ttttcatcat   360
agaaatgaag gatttgaaaa agcaggacca attaatattg cagtaatac ttggtttggc   420 ggacatgtag ccgtgcttcc gggagtgacg attggagaag cagtgtgat ggtgctggt   480 agtgttgtca ccaaagatat tccgccacac agtttagcgg ttggaaaccc ttgtaaagtc   540
gttcgtaaaa ttgataatga ggtaccatca gaagcattga acgatgaaac actaaattag   600

<210> SEQ ID NO 4
<211> LENGTH: 1560
<212> TYPE: DNA
<213> ORGANISM: Staphylococcus aureus

<400> SEQUENCE: 4
atgaatttat taagcctcct actcattttg ctggggatca ttctaggagt tgttggaggg    60
```

```
tatgttgttg cccgaaattt gttgcttcaa aagcaatcac aagctagaca aactgccgaa      120
gatattgtaa atcaagcaca taaagaagct gacaatatca aaaaagagaa attacttgag      180
gcaaaagaag aaaaccaaat cctaagagaa caaactgaag cagaactacg agaaagacgt      240
agcgaacttc aaagacaaga aacccgactt cttcaaaaag aagaaaactt agagcgtaaa      300
tctgatctat tagataaaaa agatgagatt ttagagcaaa aagaatcaaa aattgaagaa      360
aaacaacaac aagtagatgc aaaagagagt agtgttcaaa cgttaataat gaagcatgaa      420
caagaattag aacgcatctc cggtctcact caagaagaag ctattaatga gcaacttcaa      480
agagtagagg aagaactgtc acaagatatt gcagtacttg ttaaagaaaa agaaaaagaa      540
gctaaagaaa aagttgataa aacagcaaaa gaattattag ctacagcagt acaaagatta      600
gcagcagatc acacaagtga atcaacggta tcagtagtta acttacctaa tgatgagatg      660
aaaggtcgaa tcattggacg tgaaggacga acatccgta cacttgaaac tttaactggc      720
attgatttaa ttattgatga cacaccagaa gcagttatat tatctggttt tgatccaata      780
agaagagaaa ttgctagaac agcacttgtt aacttagtat ctgatggacg tattcatcca      840
ggtagaattg aagatatggt cgaaaaagct agaaaagaag tagacgatat tataagagaa      900
gcaggtgaac aagctacatt tgaagtgaac gcacataata tgcatcctga cttagtaaaa      960
attgtagggc gtttaaacta tcgtacaagt tacggtcaaa atgtacttaa acattcaatt     1020
gaagttgcgc atcttgctag tatgttagct gctgagctag gcgaagatga gacattagcg     1080
aaacgagctg acttttaca tgatgttggt aaagcaattg atcatgaagt agaaggtagt     1140
catgttgaaa tcggtgtaga attagcgaaa aaatatggtg aaaatgaaac agttattaat     1200
gcaatccatt ctcaccatgg tgatgttgaa cctacatcta ttatatctat ccttgttgct     1260
gctgcagatg cattgtctgc ggctcgtcca ggtgcaagaa aagaaacatt agagaattat     1320
attcgtcgat tagaacgttt agaaacgtta tcagaaagtt atgatggtgt agaaaaagca     1380
tttgcgattc aggcaggtag agaaatccga gtgattgtat ctcctgaaga aattgatgat     1440
ttaaaatctt atcgattggc tagagatatt aaaaatcaga ttgaagatga attacaatat     1500
cctggtcata tcaaggtgac agttgttcga gagactagag cagtagaata tgcgaaataa     1560
```

<210> SEQ ID NO 5
<211> LENGTH: 600
<212> TYPE: RNA
<213> ORGANISM: Staphylococcus aureus

<400> SEQUENCE: 5

```
augacugaaa aagaaaaaau guuagcagaa aaauggua cg augcaaacuu ugaucaagac       60
uuaaucaaug aacgugcacg agcgaaagau auuugcuuug aauuaaauca uacaaagccg      120
agugacaaaa auaaaagaaa ggaauuaauc gaugaauuau uucaaacaac aacagacaau      180
guaaguauuu cgauuccuuu ugauacagau uauggguuga acguuaaacu aggaaaaaau      240
gucuauguaa acaccaauug uuauuuuaug gaugguggac agauuacaau uggcgauaau      300
guuuuuauag gaccuaauug uggauucuac acagcaacac auccacuuaa uuucaucau       360 agaaaugaag gauuugaaaa agcaggacca auuaauauug gcaguaauac uugguuuggc      420
ggacauguag ccgugcuucc gggagugacg auuggagaag gcagugugau uggugcugguu     480 aguuuguuca ccaaagauau uccgccacac aguuuagcgg uuggaaaccc uuguaaaguc      540
guucguaaaa uugauaauga gguaccauca gaagcauuga acgaugaaac acuaaauuag      600
```

```
<210> SEQ ID NO 6
<211> LENGTH: 1560
<212> TYPE: RNA
<213> ORGANISM: Staphylococcus aureus

<400> SEQUENCE: 6
augaauuuau uaagccuccu acucauuuug cuggggauca uucuaggagu uguuggaggg      60
uauguuguug cccgaaauuu guugcuucaa aagcaaucac aagcuagaca aacugccgaa     120
gauauuguaa aucaagcaca uaaagaagcu gacaauauca aaaagagaa auuacuugag      180 gcaaaagaag aaaccaaau ccuaagagaa caaacugaag cagaacuacg agaaagacgu      240
agcgaacuuc aaagacaaga aacccgacuu cuucaaaaag aagaaaacuu agagcguaaa     300
ucugaucuau uagauaaaaa agaugagauu uuagagcaaa aagaaucaaa aauugaagaa     360
aaacaacaac aaguagaugc aaaagagagu aguguucaaa cguuaauaau gaagcaugaa     420
caagaauuag aacgcaucuc cggucucacu caagaagaag cuauuaauga gcaacuucaa     480
agaguagagg aagaacuguc acaagauauu gcaguacuug uuaaagaaaa agaaaaagaa     540
gcuaaagaaa aaguugauaa aacagcaaaa gaauuauag cuacagcagu acaaagauua     600
gcagcagauc acacaaguga aucaacggua ucaguaguua acuuaccuaa ugaugagaug     660
aaaggucgaa ucauuggacg ugaaggacga aacauccgua cacuugaaac uuuaacuggc     720
auugauuuaa uuauugauga cacaccagaa gcaguuauau uaucugguuu ugauccaaua     780
agaagagaaa uugcuagaac agcacuuguu aacuuaguau cugauggacg uauucaucca     840
gguagaauug aagauauggu cgaaaaagcu agaaaagaag uagacgauau uauaagagaa     900
gcaggugaac aagcuacauu ugaagugaac gcacauaaua ugcauccuga cuuaguaaaa     960
auuguagggc guuuaaacua ucguacaagu uacggucaaa auguacuuaa acauucaauu    1020
gaaguugcgc aucuugcuag uauguuagcu gcugagcuag gcgaagauga gacauuagcg    1080
aaacgagcug gacuuuuaca ugauguuggu aaagcaauug aucaugaagu agaagguagu    1140 caguugaaa ucgguguaga auuagcgaaa aaauauggug aaaaugaaac aguuauuaau    1200
gcaauccauu cucaccaugg ugauguugaa ccuacaucua uuauaucuau ccuuguugcu    1260
gcugcagaug cauugucugc ggcucgucca gugcaagaa agaaacauu agagaauuau    1320 auucgucgau uagaacguuu agaaacguua ucagaaaguu augauggugu agaaaaagca    1380
uuugcgauuc aggcagguag agaaauccga gugauuguau cuccgaaga aauugaugau    1440 uuaaaaucuu aucgauuggc uagagauauu aaaaaucaga uugaagauga auuacaauau    1500
ccuggucaua ucaaggugac aguuguucga gagacuagag caguagaaua ugcgaaauaa    1560
```

PROTEINS AND NUCLEIC ACIDS USEFUL IN VACCINES TARGETING *STAPHYLOCOCCUS AUREUS*

CROSS REFERENCE TO RELATED APPLICATIONS

This is a national stage filing in accordance with 35 U.S.C. § 371 of PCT/EP2017/054043, filed Feb. 22, 2017, which claims the benefit of the priority of European Patent Application No. 16156786.2, filed Feb. 22, 2016, the contents of each are incorporated herein by reference.

FIELD OF THE INVENTION

The present invention relates to the field of antimicrobial prophylaxis and therapy. In particular the present invention relates to novel proteins and polynucleotides derived from *Staphylococcus aureus*. The invention further relates to vectors comprising the polynucleotides, transformed host organisms expressing the polynucleotides, antibodies (mono- or polyclonal) specific for the polypeptides as well as diagnostic, prophylactic and therapeutic uses and methods. Finally, also methods of preparation are part of the invention.

BACKGROUND OF THE INVENTION

Bacterial infections are in most instances successfully treated by administration of antibiotics to patients in need thereof. However, due to careless or thoughtless use of powerful antibiotics, many pathological germs become resistant against antibiotics over time. One threatening example is *Staphylococcus aureus*. In particular in hospitals this bacterium is of relevance. So-called Methicillin Resistant *S. Aureus* (MRSA) strains jeopardize patient's survival in hospitals, in particular after surgery.

Vaccination is considered to be a very effective method of preventing infectious diseases in human and veterinary health care. Vaccination is the administration of immungenically effective amounts of antigenic material (the vaccine) to produce immunity to a disease/disease-causing pathogenic agent. Vaccines have contributed to the eradication of smallpox, the near eradication of polio, and the control of a variety of diseases, including rubella, measles, mumps, chickenpox, typhoid fever.

Before "the genomic era", vaccines were based on killed or live attenuated, microorganisms, or parts purified from them. Subunit vaccines are considered as a modern upgrade of these types of vaccine, as the subunit vaccines contain one or more protective antigens, which are more or less the weak spot of the pathogen. Hence, in order to develop subunit vaccines, it is critical to identify the proteins, which are important for inducing protection and to eliminate others.

An antigen is said to be protective if it is able to induce protection from subsequent challenge by a disease-causing infectious agent in an appropriate animal model following immunization.

The empirical approach to subunit vaccine development, which includes several steps, begins with pathogen cultivation, followed by purification into components, and then testing of antigens for protection. Apart from being time and labour consuming, this approach has several limitations that can lead to failure. It is not possible to develop vaccines using this approach for microorganisms, which cannot easily be cultured and only allows for the identification of the antigens, which can be obtained in sufficient quantities. The empirical approach has a tendency to focus on the most abundant proteins, which in some cases are not immunoprotective. In other cases, the antigen expressed during in vivo infection is not expressed during in vitro cultivation. Furthermore, antigen discovery by use of the empirical approach demands an extreme amount of proteins in order to discover the protective antigens, which are like finding needles in the haystack. This renders it a very expensive approach, and it limits the vaccine development around diseases, which is caused by pathogens with a large genome or disease areas, which perform badly in a cost-effective perspective.

OBJECT OF THE INVENTION

It is an object of embodiments of the invention to provide *S. aureus* derived antigenic polypeptides that may serve as constituents in vaccines against *S. aureus* infections and in diagnosis of *S. aureus* infections. It is also an object to provide nucleic acids, vectors, transformed cells, vaccine compositions, and other useful means for molecular cloning as well as for therapy and diagnosis with relevance for *S. aureus*.

SUMMARY OF THE INVENTION

It has been found by the present inventor(s) that *S. aureus*, in particular drug resistant *S. aureus*, expresses a number of hitherto unknown putatively surface exposed proteins which are candidates as vaccine targets as well as candidates as immunizing agents for preparation of antibodies that target *S. aureus*.

The present assignee has previously filed patent applications relating to a number of immunogenic peptides form *S. aureus*. The polypeptides of the present invention are useful as (vaccine) immunogens per se but also in combination with any one of the immunogens disclosed in WO 2012/136653 and/or WO 2015/053899.

So, in a first aspect the present invention relates to a polypeptide comprising
a) an amino acid sequence selected from the group consisting of any one of SEQ ID NO: 1 and SEQ ID NO: 2, or
b) an amino acid sequence consisting of at least or exactly or at most 5 contiguous amino acid residues from SEQ ID NO: 1 or 2, or
c) an amino acid sequence having a sequence identity of at least 60% with the amino acid sequence of a),
d) an amino acid sequence having a sequence identity of at least 60% with the amino acid sequence of b), or
e) an assembly of amino acids derived from any one of SEQ ID NOs: 1-2, which has essentially the same 3D conformation as in the protein from which said assembly is derived so as to constitute a B-cell epitope, said polypeptide being antigenic in a mammal.

In another aspect, the invention relates to an isolated nucleic acid fragment, which comprises
i) a nucleotide sequence encoding a polypeptide of the invention, or
ii) a nucleotide sequence consisting of any one of SEQ ID NOs: 3-6.
iii) a nucleotide sequence consisting of at least or exactly or at most 10 consecutive nucleotides in any one of SEQ ID NOs: 3-6,
iv) a nucleotide sequence having a sequence identity of at least 60% with the nucleotide sequence in i) or ii),
v) a nucleotide sequence having a sequence identity of at least 60% with the nucleotide sequence in iii), vi) a nucleotide sequence complementary to the nucleotide sequence in i)-v), or vii) a nucleotide sequence which hybridizes under stringent conditions with the nucleotide sequence in i)-vi).

In a third aspect, the invention relates to a vector comprising the nucleic acid of the invention, such as a cloning vector or an expression vector.

In fourth aspect, the invention relates to a cell which is transformed so as to carry the vector of the invention.

In a fifth aspect, the invention relates to a pharmaceutical composition comprising a polypeptide of the invention, a nucleic acid fragment of the invention, a vector of the invention, or a transformed cell of the invention, and a pharmaceutically acceptable carrier, vehicle or diluent.

In a sixth aspect, the invention relates to a method for inducing immunity in an animal by administering at least once an immunogenically effective amount of a polypeptide of the invention, a nucleic acid fragment of the invention, a vector of the invention, a transformed cell of the invention, or a pharmaceutical composition of the fifth aspect of the invention so as to induce adaptive immunity against S. aureus in the animal.

In a seventh and eighth aspect, the invention relates to 1) a polyclonal antibody in which the antibodies specifically bind to at least one polypeptide of the invention, and which is essentially free from antibodies binding specifically to other S. aureus polypeptides, and to 2) an isolated monoclonal antibody or antibody analogue which binds specifically to a polypeptide of the invention. In a related ninth aspect, the invention relates to a pharmaceutical composition comprising such a polyclonal or monoclonal antibody and a pharmaceutically acceptable carrier, vehicle or diluent.

In a $10^{th}$ aspect, the invention relates to a method for prophylaxis, treatment or amelioration of infection with S. aureus, comprising administering a therapeutically effective amount of an antibody of the $7^{th}$ or $8^{th}$ aspect of the invention or a pharmaceutical composition of the eighth aspect to an individual in need thereof.

In an $11^{th}$ aspect, the invention relates to a method for determining, quantitatively or qualitatively, the presence of S. aureus, in particular the presence of multi-resistant S. aureus, in a sample, the method comprising contacting the sample with an antibody of aspects 8 or 9 of the invention and detecting the presence of antibody bound to material in the sample.

In an $12^{th}$ aspect of the invention is provided a method for determining, quantitatively or qualitatively, the presence of antibodies specific for S. aureus, in particular the presence of antibodies specific for multi-resistant S. aureus, in a sample, the method comprising contacting the sample with a polypeptide of the invention and detecting the presence of antibody that specifically bind said polypeptide.

In a $13^{th}$ aspect, the invention relates to a method for determining, quantitatively or qualitatively, the presence of a nucleic acid characteristic of S. aureus, in particular the presence of a nucleic acid characteristic of multi-resistant S. aureus, in a sample, the method comprising contacting the sample with a nucleic acid fragment of the invention and detecting the presence of nucleic acid in the sample that hybridizes to said nucleic acid fragment.

In a $14^{th}$ aspect, the invention relates to a method for the preparation of the polypeptide of the invention, comprising
culturing a transformed cell of the present invention, which is capable of expressing the nucleic acid of the invention, under conditions that facilitate that the transformed cell expresses the nucleic acid fragment of the invention, which encodes a polypeptide of the invention, and subsequently recovering said polypeptide, or preparing said polypeptide by means of solid or liquid phase peptide synthesis.

In a $15^{th}$ aspect, the invention relates to a method for determining whether a substance, such as an antibody, is potentially useful for treating infection with S. aureus, the method comprising contacting the polypeptide of the invention with the substance and subsequently establishing whether the substance has at least one of the following characteristics:

1) the ability to bind specifically to said polypeptide,
2) the ability to compete with said polypeptide for specific binding to a ligand/receptor, and
3) the ability to specifically inactivate said polypeptide.

Finally, in a $16^{th}$ aspect, the invention relates to a method for determining whether a substance, such as a nucleic acid, is potentially useful for treating infection with S. aureus, the method comprising contacting the substance with the nucleic acid fragment of claim of the invention and subsequently establishing whether the substance has either the ability to 1) bind specifically to the nucleic acid fragment, or
2) bind specifically to a nucleic acid that hybridizes specifically with the nucleic acid fragment.

LEGENDS TO THE FIGURES

FIG. 1: Survival of mice immunized with SAR1262-25-519.

The survival of mice immunized with SAR1262-25-519 was significantly different from that of mice in the control group. 86% of the SAR1262-25-519 immunized mice survived the lethal S. aureus challenge, which was significantly different from the 17% survival of the control group. The data were analysed using log-rank (Mantel-Cox) test, 2=0.0322.

Figure 2:
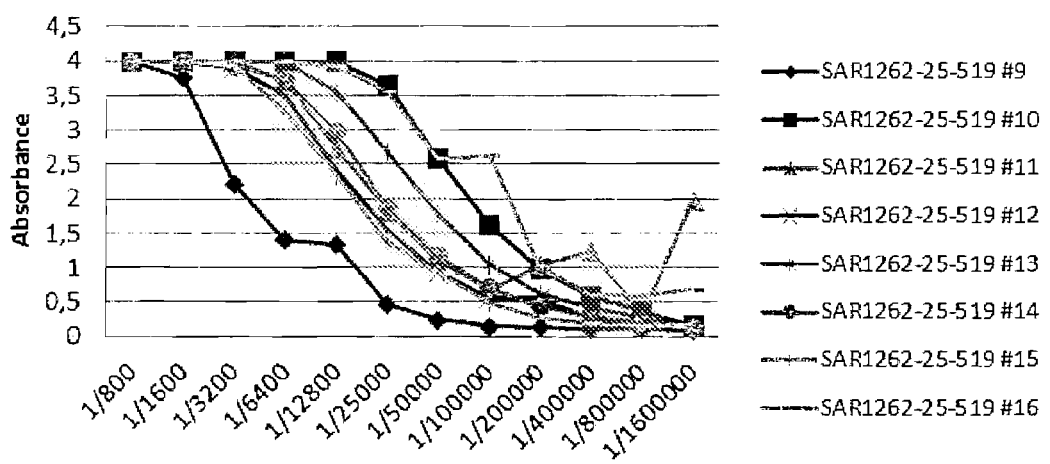

FIG. 2: Antibody production against SAR1262-25-519 in 8 immunized mice.

The antibody titre was measured in plasma from the 8 mice immunized with SAR1262-25-519. Each curve represents the antibody titre of one mouse, see #ID number in the figure. The Y-axis represents the absorbance measured at 490 nm-650 nm (reference), and the X-axis shows the plasma dilution. There was some variation in the antibody responses to SAR1262-25-519. Mouse #16 had to be euthanized prior to challenge.

Figure 3:
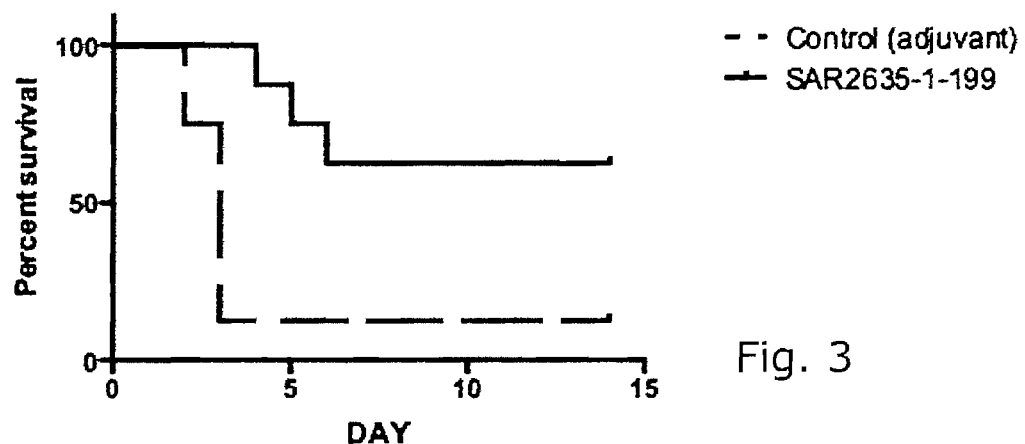

FIG. 3: Survival of mice immunized with SAR2635-1-199.

The survival of mice immunized with SAR2635-1-199 was significantly higher than that of mice in the control group. 63% of the SAR2635-1-199 immunized mice survived the lethal S. aureus challenge compared to 13% survival of the control group. The data were analysed using log-rank (Mantel-Cox) test, P=0.0067.

Figure 4:
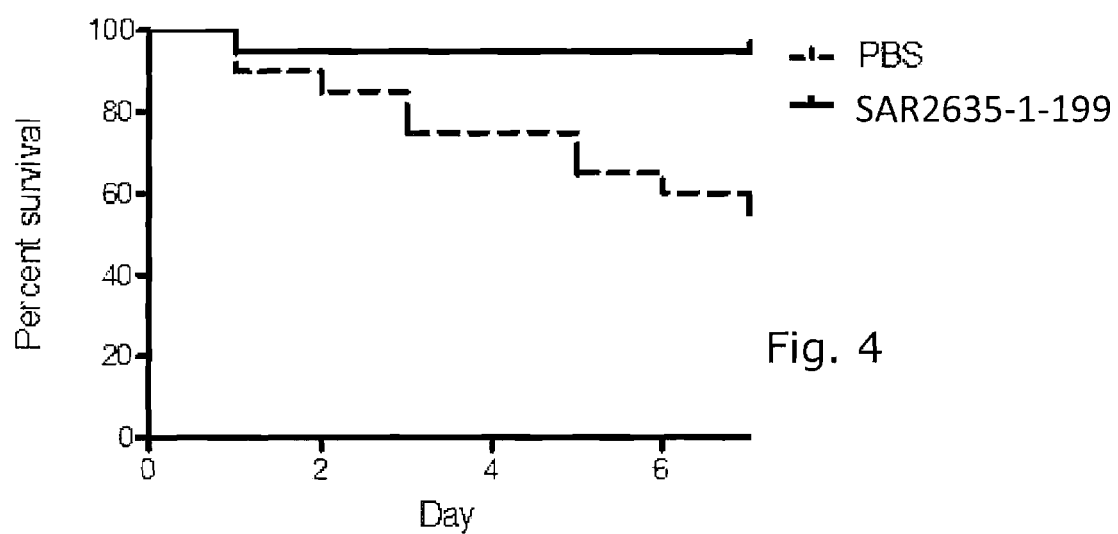

FIG. 4: Survival of mice immunized with SAR2635-1-199.

The survival of mice immunized with SAR2635-1-199 was significantly higher than that of mice in the control group. 95% of the 5AR2635-1-199 immunized mice survived the lethal S. aureus challenge, compared to 55% survival of the control group. The data were analysed using log-rank (Mantel-Cox) test, P=0.0046.

Figure 5:
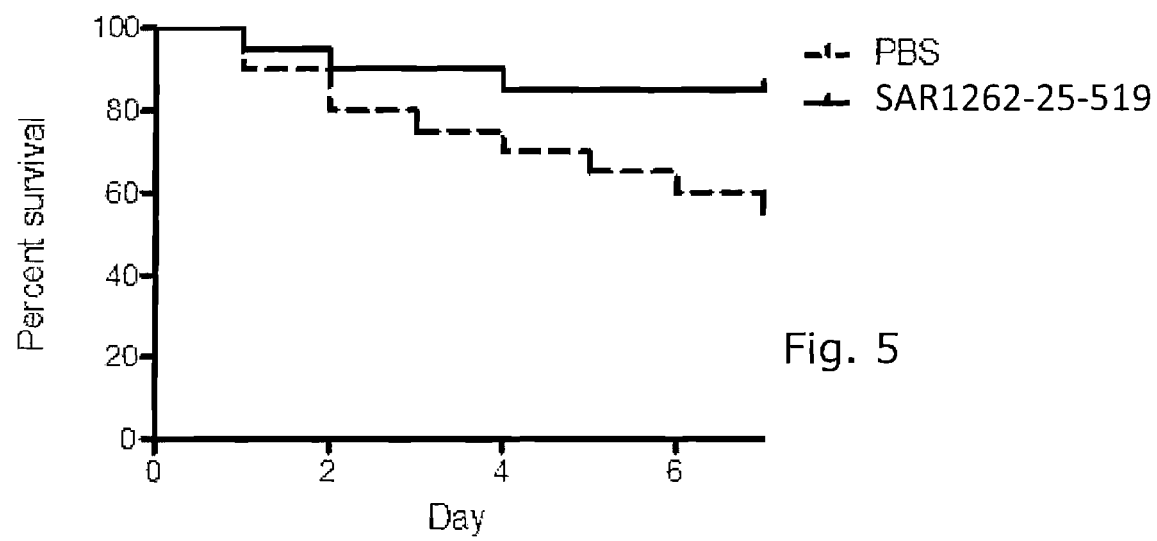

FIG. 5: Survival of mice immunized with SAR1262-25-519.

The survival of mice immunized with SAR1262-25-519 was significantly higher than that of mice in the control group. 85% of the SAR1262-25-519 immunized mice survived the lethal *S. aureus* challenge, compared to 55% survival of the control group. The data were analysed using log-rank (Mantel-Cox) test, P=0.0478.

DETAILED DISCLOSURE OF THE INVENTION

Definitions

The term "polypeptide" is in the present context intended to mean both short peptides of from 2 to 10 amino acid residues, oligopeptides of from 11 to 100 amino acid residues, and polypeptides of more than 100 amino acid residues. Further-more, the term is also intended to include proteins, i.e.□functional biomolecules comprising at least one polypeptide; when comprising at least two polypeptides, these may form complexes, be covalently linked, or may be non-covalently linked. The polypeptide (s) in a protein can be glycosylated and/or lipidated and/or comprise prosthetic groups.

The term "subsequence" means any consecutive stretch of at least 3 amino acids or, when relevant, of at least 3 nucleotides, derived directly from a naturally occurring amino acid sequence or nucleic acid sequence, respectively The term "amino acid sequence" designates the order in which amino acid residues, connected by peptide bonds, lie in the chain in peptides and proteins.

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"Sequence identity" is in the context of the present invention determined by comparing 2 optimally aligned sequences of equal length (e.g. DNA, RNA or amino acid) according to the following formula: $(N_{ref}-N_{dif}) \cdot 100/N_{ref}$, wherein $N_{ref}$ is the number of residues in one of the 2 sequences and $N_{dif}$ is the number of residues which are non-identical in the two sequences when they are aligned over their entire lengths and in the same direction. So, two sequences 5'-ATTCGGAACC-3' and 5'-ATACGGGACC-3' will provide the sequence identity 80% ($N_{ref}=10$ and $N_{dif}=2$).

An "assembly of amino acids" means two or more amino acids bound together by physical or chemical means.

The "3D conformation" is the 3 dimensional structure of a biomolecule such as a protein. In monomeric polypeptides/proteins, the 3D conformation is also termed "the tertiary structure" and denotes the relative locations in 3 dimensional space of the amino acid residues forming the polypeptide.

"An immunogenic carrier" is a molecule or moiety to which an immunogen or a hapten can be coupled in order to enhance or enable the elicitation of an immune response against the immunogen/hapten. Immunogenic carriers are in classical cases relatively large molecules (such as tetanus toxoid, KLH, diphtheria toxoid etc.) which can be fused or conjugated to an immunogen/hapten, which is not sufficiently immunogenic in its own right-typically, the immunogenic carrier is capable of eliciting a strong T-helper lymphocyte response against the combined substance constituted by the immunogen and the immunogenic carrier, and this in turn provides for improved responses against the immunogen by B-lymphocytes and cytotoxic lymphocytes. More recently, the large carrier molecules have to a certain extent been substituted by so-called promiscuous T-helper epitopes, i.e. shorter peptides that are recognized by a large fraction of HLA haplotypes in a population, and which elicit T-helper lymphocyte responses.

A "T-helper lymphocyte response" is an immune response elicited on the basis of a peptide, which is able to bind to an MHC class II molecule (e.g. an HLA class II molecule) in an antigen-presenting cell and which stimulates T-helper lymphocytes in an animal species as a consequence of T-cell receptor recognition of the complex between the peptide and the MHC Class II molecule presenting the peptide.

An "immunogen" is a substance of matter which is capable of inducing an adaptive immune response in a host, whose immune system is confronted with the immunogen. As such, immunogens are a subset of the larger genus "antigens", which are substances that can be recognized specifically by the immune system (e.g. when bound by antibodies or, alternatively, when fragments of the are antigens bound to MHC molecules are being recognized by T-cell receptors) but which are not necessarily capable of inducing immunity—an antigen is, however, always capable of eliciting immunity, meaning that a host that has an established memory immunity against the antigen will mount a specific immune response against the antigen.

A "hapten" is a small molecule, which can neither induce nor elicit an immune response, but if conjugated to an immunogenic carrier, antibodies or TCRs that recognize the hapten can be induced upon confrontation of the immune system with the hapten carrier conjugate.

An "adaptive immune response" is an immune response in response to confrontation with an antigen or immunogen, where the immune response is specific for antigenic determinants of the antigen/immunogen—examples of adaptive immune responses are induction of antigen specific antibody production or antigen specific induction/activation of T helper lymphocytes or cytotoxic lymphocytes.

A "protective, adaptive immune response" is an antigen-specific immune response induced in a subject as a reaction to immunization (artificial or natural) with an antigen, where the immune response is capable of protecting the subject against subsequent challenges with the antigen or a pathology-related agent that includes the antigen. Typically, prophylactic vaccination aims at establishing a protective adaptive immune response against one or several pathogens.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen.

Hybridization under "stringent conditions" is herein defined as hybridization performed under conditions by which a probe will hybridize to its target sequence, to a detectably greater degree than to other sequences. Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

The term "animal" is in the present context in general intended to denote an animal species (preferably mammalian), such as *Homo sapiens, Canis domesticus*, etc. and not just one single animal. However, the term also denotes a population of such an animal species, since it is important that the individuals immunized according to the method of the invention substantially all will mount an immune response against the immunogen of the present invention.

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

"Specific binding" denotes binding between two substances which goes beyond binding of either substance to randomly chosen substances and also goes beyond simple association between substances that tend to aggregate because they share the same overall hydrophobicity or hydrophilicity. As such, specific binding usually involves a combination of electrostatic and other interactions between two conformationally complementary areas on the two substances, meaning that the substances can "recognize" each other in a complex mixture.

The term "vector" is used to refer to a carrier nucleic acid molecule into which a heterologous nucleic acid sequence can be inserted for introduction into a cell where it can be replicated and expressed. The term further denotes certain biological vehicles useful for the same purpose, e.g. viral vectors and phage—both these infectious agents are capable of introducing a heterologous nucleic acid sequence The term "expression vector" refers to a vector containing a nucleic acid sequence coding for at least part of a gene product capable of being transcribed. In some cases, when the transcription product is an RNA molecule such as an mRNA molecule, this is in turn translated into a protein, polypeptide, or peptide.

SPECIFIC EMBODIMENTS OF THE INVENTION

The Polypeptides of the Invention

In some embodiments the at least or exactly 5 contiguous amino acids referred to in option b) in the definition of the first aspect of the invention constitute at least or exactly or at most 6 contiguous amino acid residues, such as at least or exactly or at most 7, at least or exactly or at most 8, at least or exactly or at most 9, at least or exactly or at most 10, at least or exactly or at most 11, at least or exactly or at most 12, at least or exactly or at most 13, at least or exactly or at most 14, at least or exactly or at most 15, at least or exactly or at most 16, at least or exactly or at most 17, at least or exactly or at most 18, at least or exactly or at most 19, at least or exactly or at most 20, at least or exactly or at most 21, at least or exactly or at most 22, at least or exactly or at most 23, at least or exactly or at most 24, at least or exactly or at most 25, at least or exactly or at most 26, at least or exactly or at most 27 at least or exactly or at most 28, at least or exactly or at most 29, at least or exactly or at most 30, at least or exactly or at most 31, at least or exactly or at most 32, at least or exactly or at most 33, at least or exactly or at most 34, at least or exactly or at most 35, at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, or at least or exactly or at most 198 contiguous amino acid residues of SEQ ID NO: 1.

In some embodiments the at least or exactly 5 contiguous amino acids referred to in option b) in the definition of the first aspect of the invention constitute at least or exactly or at most 6 contiguous amino acid residues, such as at least or exactly or at most 7, at least or exactly or at most 8, at least or exactly or at most 9, at least or exactly or at most 10, at least or exactly or at most 11, at least or exactly or at most 12, at least or exactly or at most 13, at least or exactly or at most 14, at least or exactly or at most 15, at least or exactly or at most 16, at least or exactly or at most 17, at least or exactly or at most 18, at least or exactly or at most 19, at least or exactly or at most 20, at least or exactly or at most 21, at least or exactly or at most 22, at least or exactly or at most 23, at least or exactly or at most 24, at least or exactly or at most 25, at least or exactly or at most 26, at least or exactly or at most 27 at least or exactly or at most 28, at least or exactly or at most 29, at least or exactly or at most 30, at least or exactly or at most 31, at least or exactly or at most 32, at least or exactly or at most 33, at least or exactly or at most 34, at least or exactly or at most 35, at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 261, at least or exactly or at most 262, at least or exactly or at most 263, at least or exactly or at most 264, at least or exactly or at most 265, at least or exactly or at most 266, at least or exactly or at most 267, at least or exactly or at most 268, at least or exactly or at most 269, at least or exactly or at most 270, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, at least or exactly or at most 319, at least or exactly or at most 320, at least or exactly or at most 321, at least or exactly or at most 322, at least or exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, at least or exactly or at most 351, at least or exactly or at most 352, at least or exactly or at most 353, at least or exactly or at most 354, at least or exactly or at most 355, at least or exactly or at most 356, at least or exactly or at most 357, at least or exactly or at most 358, at least or exactly or at most 359, at least or exactly or at most 360, at least or exactly or at most 361, at least or exactly or at most 362, at least or exactly or at most 363, at least or exactly or at most 364, at least or exactly or at most 365, at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, at least or exactly or at most 390, at least or exactly or at most 391, at least or exactly or at most 392, at least or exactly or at most 393, at least or exactly or at most 394, at least or exactly or at most 395, at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, at least or exactly or at most 404, at least or exactly or at most 405, at least or exactly or at most 406, at least or exactly or at most 407, at least or exactly or at most 408, at least or exactly or at most 409, at least or exactly or at most 410, at least or exactly or at most 411, at least or exactly or at most 412, at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420, at least or exactly or at most 421, at least or exactly or at most 422, at least or exactly or at most 423, at least or exactly or at most 424, at least or exactly or at most 425, at least or exactly or at most 426, at least or exactly or at most 427, at least or exactly or at most 428, at least or exactly or at most 429, at least or exactly or at most 430, at least or exactly or at most 431, at least or exactly or at most 432, at least or exactly or at most 433, at least or exactly or at most 434, at least or exactly or at most 435, at least or exactly or at most 436, at least or exactly or at most 437, at least or exactly or at most 438, at least or exactly or at most 439, at least or exactly or at most 440, at least or exactly or at most 441, at least or exactly or at most 442, at least or exactly or at most 443, at least or exactly or at most 444, at least or exactly or at most 445, at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, at least or exactly or at most 458, at least or exactly or at most 459, at least or exactly or at most 460, at least or exactly or at most 461, at least or exactly or at most 462, at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, at least or exactly or at most 473, at least or exactly or at most 474, at least or exactly or at most 475, at least or exactly or at most 476, at least or exactly or at most 477, at least or exactly or at most 478, at least or exactly or at most 479, at least or exactly or at most 480, at least or exactly or at most 481, at least or exactly or at most 482, at least or exactly or at most 483, at least or exactly or at most 484, at least or exactly or at most 485, at least or exactly or at most 486, at least or exactly or at most 487, at least or exactly or at most 488, at least or exactly or at most 489, at least or exactly or at most 490, at least or exactly or at most 491, at least or exactly or at most 492, at least or exactly or at most 493, at least or exactly or at most 494, at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506, at least or exactly or at most 507, at least or exactly or at most 508, at least or exactly or at most 509, at least or exactly or at most 510, at least or exactly or at most 511, at least or exactly or at most 512, at least or exactly or at most 513, at least or exactly or at most 514, at least or exactly or at most 515, at least or exactly or at most 516, at least or exactly or at most 517, or at least or exactly or at most 518 contiguous amino acid residues of SEQ ID NO: 2.

Another way to phrase this is that for each of SEQ ID NOs: 1 and 2 the number of the contiguous amino acid residues is at least or exactly or at most N-n, where N is the length of the sequence ID in question and n is any integer between N-5 and 0; that is, the at least 5 contiguous amino acids can be at least any number between 5 and the length of the reference sequence minus one, in increments of one.

In some embodiments, the polypeptide of the invention also has a sequence identity with the amino acid sequence of a) defined above of at least 61%, such as at least 63%, at least 63% at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81,%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, and at least 99%. Similarly, the polypeptide of the invention in some embodiments also has a sequence identity with the amino acid sequence of b) defined above of at least 61%, such as at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81,%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, and at least 99%.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 43, 44, 45, 46, 47, 48, 49, 50, 51, 52, 53, 54, 55, 56, 57, 58, 59, 60, 61, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 171, 172, 173, 174, 175, 176, 177, 178, 179, 180, 181, 182, 183, 184, 185, 186, 187, 188, 189, 190, 191, 192, 193, 194, and 195 in SEQ ID NO: 1 or 2, if the number of the at least or exactly or at most 5 amino acid residues so permit—if the number of the at least or exactly or at most 5 amino acids is higher than 5, the N-terminal first residue will not be higher numbered than N-L+1, where N is the number of amino acid residues of the reference sequence and L is the number of amino acids defined for option b. For instance, if the number of the contiguous amino acid residues defined in option b is exactly 30 and the sequence in question is SEQ ID NO: 1, the N-terminal first residue can hence not be higher numbered than 199−30+1=170, meaning that the 30 amino acid residues in that case will be constituted by amino acid residues 170-199 of SEQ ID NO: 1.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510 and 511, 512, 513, 514, and 515 in SEQ ID NO: 2, if the number of the at least or exactly or at most 5 amino acid residues so permit—if the number of the at least or exactly or at most 5 amino acids is higher than 5, the N-terminal first residue will not be higher numbered than N-L+1, where N is the number of amino acid residues of the reference sequence and L is the number of amino acids defined for option b. For instance, if the number of the contiguous amino acid residues defined in option b is exactly 30 and the sequence in question is SEQ ID NO: 2, the N-terminal first residue can hence not be higher numbered than 519-30+1=490, meaning that the 30 amino acid residues in that case will be constituted by amino acid residues 490-519 of SEQ ID NO: 2.

The polypeptide of the invention is in certain embodiments also fused or conjugated to an immunogenic carrier molecule; or, phrased otherwise, the polypeptide of the invention also includes such an immunogenic carrier molecule in addition to the material derived from SEQ ID NO: 1 or 2. The immunogenic carrier molecule is a typically polypeptide that induces T-helper lymphocyte responses in a majority of humans, such as immunogenic carrier proteins selected from the group consisting of keyhole limpet hemocyanin or a fragment thereof, tetanus toxoid or a fragment thereof, diphtheria toxoid or a fragment thereof. Other suitable carrier molecules are discussed infra. One further fusion partner, which is preferably incorporated is a "His tag", i.e. a stretch of amino acids, which is rich or only consists of histidinyl residues so as to facilitate protein purification.

In preferred embodiments, the polypeptide of the invention detailed above is capable of inducing an adaptive immune response against the polypeptide in a mammal, in particular in a human being. Preferably, the adaptive immune response is a protective adaptive immune response against infection with S. aureus, in particular multi-resistant S. aureus. The polypeptide may in these cases induce a humeral and/or a cellular immune response.

Epitopes

SEQ ID NOs: 1 and 2 include an determinants (epitopes) that are as such recognized by antibodies and/or when bound to MHC molecules by T-cell receptors. For the purposes of the present invention, B-cell epitopes (i.e. antibody binding epitopes) are of particular relevance.

It is relatively uncomplicated to identify linear B-cell epitopes—one very simple approach entails that antibodies raised against S. aureus or S. aureus derived proteins disclosed herein are tested for binding to overlapping oligomeric peptides derived from SEQ ID NO: 1 or 2. Thereby, the regions of the S. aureus polypeptide which are responsible for or contribute to binding to the antibodies can be identified.

Alternatively, or additionally, one can produce mutated versions of the polypeptides of the invention, e.g. version where each single non-alanine residue in SEQ ID NO: 1 or 2 are point mutated to alanine—this method also assists in identifying complex assembled B-cell epitopes; this is the case when binding of the same antibody is modified by exchanging amino acids in different areas of the full-length polypeptide.

Also, in silico methods for B-cell epitope prediction can be employed: useful state-of-the-art systems for β-turn prediction is provided in Petersen B et al. (November 2010), Plos One 5(11): e15079; prediction of linear B-cell epitopes, cf.: Larsen 3 E P et al. (April 2006), Immunome Research, 2:2; prediction of solvent exposed amino acids: Petersen B et al (July 2009), BMC Structural Biology, 9:51.

The Nucleic Acid Fragments of the Invention

The nucleic acid fragment of the invention referred to above is preferably is a DNA fragment (such as SEQ ID NOs: 3 and 4) or an RNA fragment (such as SEQ ID NOs 5 or 6).

The nucleic acid fragment of the invention typically consists of at least or exactly or at most at least or exactly or at most 11, such as at least or exactly or at most 12, at least or exactly or at most 13, at least or exactly or at most 14, at least or exactly or at most 15, at least or exactly or at most 16, at least or exactly or at most 17 at least or exactly or at most 18, at least or exactly or at most 19, at least or exactly or at most 20, at least or exactly or at most 21, at least or exactly or at most 22, at least or exactly or at most 23, at least or exactly or at most 24, at least or exactly or at most 25, at least or exactly or at most 26, at least or exactly or at most 27, at least or exactly or at most 28, at least or exactly or at most 29, at least or exactly or at most 30, at least or exactly or at most 31, at least or exactly or at most 32, at least or exactly or at most 33, at least or exactly or at most 34, at least or exactly or at most 35, at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, at least or exactly or at most 319, at least or exactly or at most 320, at least or exactly or at most 321, at least or exactly or at most 322, at least or exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, at least or exactly or at most 351, at least or exactly or at most 352, at least or exactly or at most 353, at least or exactly or at most 354, at least or exactly or at most 355, at least or exactly or at most 356, at least or exactly or at most 357, at least or exactly or at most 358, at least or exactly or at most 359, at least or exactly or at most 360, at least or exactly or at most 361, at least or exactly or at most 362, at least or exactly or at most 363, at least or exactly or at most 364, at least or exactly or at most 365, at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, at least or exactly or at most 390, at least or exactly or at most 391, at least or exactly or at most 392, at least or exactly or at most 393, at least or exactly or at most 394, at least or exactly or at most 395, at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, at least or exactly or at most 404, at least or exactly or at most 405, at least or exactly or at most 406, at least or exactly or at most 407, at least or exactly or at most 408, at least or exactly or at most 409, at least or exactly or at most 410, at least or exactly or at most 411, at least or exactly or at most 412, at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420, at least or exactly or at most 421, at least or exactly or at most 422, at least or exactly or at most 423, at least or exactly or at most 424, at least or exactly or at most 425, at least or exactly or at most 426, at least or exactly or at most 427, at least or exactly or at most 428, at least or exactly or at most 429, at least or exactly or at most 430, at least or exactly or at most 431, at least or exactly or at most 432, at least or exactly or at most 433, at least or exactly or at most 434, at least or exactly or at most 435, at least or exactly or at most 436, at least or exactly or at most 437, at least or exactly or at most 438, at least or exactly or at most 439, at least or exactly or at most 440, at least or exactly or at most 441, at least or exactly or at most 442, at least or exactly or at most 443, at least or exactly or at most 444, at least or exactly or at most 445, at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, at least or exactly or at most 458, at least or exactly or at most 459, at least or exactly or at most 460, at least or exactly or at most 461, at least or exactly or at most 462, at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, at least or exactly or at most 473, at least or exactly or at most 474, at least or exactly or at most 475, at least or exactly or at most 476, at least or exactly or at most 477, at least or exactly or at most 478, at least or exactly or at most 479, at least or exactly or at most 480, at least or exactly or at most 481, at least or exactly or at most 482, at least or exactly or at most 483, at least or exactly or at most 484, at least or exactly or at most 485, at least or exactly or at most 486, at least or exactly or at most 487, at least or exactly or at most 488, at least or exactly or at most 489, at least or exactly or at most 490, at least or exactly or at most 491, at least or exactly or at most 492, at least or exactly or at most 493, at least or exactly or at most 494, at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506, at least or exactly or at most 507, at least or exactly or at most 508, at least or exactly or at most 509, at least or exactly or at most 510, at least or exactly or at most 511, at least or exactly or at most 512, at least or exactly or at most 513, at least or exactly or at most 514, at least or exactly or at most 515, at least or exactly or at most 516, at least or exactly or at most 517, at least or exactly or at most 518, at least or exactly or at most 519, at least or exactly or at most 520, at least or exactly or at most 521, at least or exactly or at most 522, at least or exactly or at most 523, at least or exactly or at most 524, at least or exactly or at most 525, at least or exactly or at most 526, at least or exactly or at most 527, at least or exactly or at most 528, at least or exactly or at most 529, at least or exactly or at most 530, at least or exactly or at most 531, at least or exactly or at most 532, at least or exactly or at most 533, at least or exactly or at most 534, at least or exactly or at most 535, at least or exactly or at most 536, at least or exactly or at most 537, at least or exactly or at most 538, at least or exactly or at most 539, at least or exactly or at most 540, at least or exactly or at most 541, at least or exactly or at most 542, at least or exactly or at most 543, at least or exactly or at most 544, at least or exactly or at most 545, at least or exactly or at most 546, at least or exactly or at most 547, at least or exactly or at most 548, at least or exactly or at most 549, at least or exactly or at most 550, at least or exactly or at most 551, at least or exactly or at most 552, at least or exactly or at most 553, at least or exactly or at most 554, at least or exactly or at most 555, at least or exactly or at most 556, at least or exactly or at most 557, at least or exactly or at most 558, at least or exactly or at most 559, at least or exactly or at most 560, at least or exactly or at most 561, at least or exactly or at most 562, at least or exactly or at most 563, at least or exactly or at most 564, at least or exactly or at most 565, at least or exactly or at most 566, at least or exactly or at most 567, at least or exactly or at most 568, at least or exactly or at most 569, at least or exactly or at most 570, at least or exactly or at most 571, at least or exactly or at most 572, at least or exactly or at most 573, at least or exactly or at most 574, at least or exactly or at most 575, at least or exactly or at most 576, at least or exactly or at most 577, at least or exactly or at most 578, at least or exactly or at most 579, at least or exactly or at most 580, at least or exactly or at most 581, at least or exactly or at most 582, at least or exactly or at most 583, at least or exactly or at most 584, at least or exactly or at most 585, at least or exactly or at most 586, at least or exactly or at most 587, at least or exactly or at most 588, at least or exactly or at most 589, at least or exactly or at most 590, at least or exactly or at most 591, at least or exactly or at most 592, at least or exactly or at most 593, at least or exactly or at most 594, at least or exactly or at most 595, at least or exactly or at most 596, at least or exactly or at most 597, at least or exactly or at most 598, at least or exactly or at most 599 consecutive nucleotides in the part of the reading frame beginning with residue 1 of SEQ ID NO: 3, 4, 5, or 6 (i.e. that encodes amino acids).

The nucleic acid fragment of the invention can also consist of at least or exactly or at most 600, at least or exactly or at most 601, at least or exactly or at most 602, at least or exactly or at most 603, at least or exactly or at most 604, at least or exactly or at most 605, at least or exactly or at most 606, at least or exactly or at most 607, at least or exactly or at most 608, at least or exactly or at most 609, at least or exactly or at most 610, at least or exactly or at most 611, at least or exactly or at most 612, at least or exactly or at most 613, at least or exactly or at most 614, at least or exactly or at most 615, at least or exactly or at most 616, at least or exactly or at most 617, at least or exactly or at most 618, at least or exactly or at most 619, at least or exactly or at most 620, at least or exactly or at most 621, at least or exactly or at most 622, at least or exactly or at most 623, at least or exactly or at most 624, at least or exactly or at most 625, at least or exactly or at most 626, at least or exactly or at most 627, at least or exactly or at most 628, at least or exactly or at most 629, at least or exactly or at most 630, at least or exactly or at most 631, at least or exactly or at most 632, at least or exactly or at most 633, at least or exactly or at most 634, at least or exactly or at most 635, at least or exactly or at most 636, at least or exactly or at most 637, at least or exactly or at most 638, at least or exactly or at most 639, at least or exactly or at most 640, at least or exactly or at most 641, at least or exactly or at most 642, at least or exactly or at most 643, at least or exactly or at most 644, at least or exactly or at most 645, at least or exactly or at most 646, at least or exactly or at most 647, at least or exactly or at most 648, at least or exactly or at most 649, at least or exactly or at most 650, at least or exactly or at most 651, at least or exactly or at most 652, at least or exactly or at most 653, at least or exactly or at most 654, at least or exactly or at most 655, at least or exactly or at most 656, at least or exactly or at most 657, at least or exactly or at most 658, at least or exactly or at most 659, at least or exactly or at most 660, at least or exactly or at most 661, at least or exactly or at most 662, at least or exactly or at most 663, at least or exactly or at most 664, at least or exactly or at most 665, at least or exactly or at most 666, at least or exactly or at most 667, at least or exactly or at most 668, at least or exactly or at most 669, at least or exactly or at most 670, at least or exactly or at most 671, at least or exactly or at most 672, at least or exactly or at most 673, at least or exactly or at most 674, at least or exactly or at most 675, at least or exactly or at most 676, at least or exactly or at most 677, at least or exactly or at most 678, at least or exactly or at most 679, at least or exactly or at most 680, at least or exactly or at most 681, at least or exactly or at most 682, at least or exactly or at most 683, at least or exactly or at most 684, at least or exactly or at most 685, at least or exactly or at most 686, at least or exactly or at most 687, at least or exactly or at most 688, at least or exactly or at most 689, at least or exactly or at most 690, at least or exactly or at most 691, at least or exactly or at most 692, at least or exactly or at most 693, at least or exactly or at most 694, at least or exactly or at most 695, at least or exactly or at most 696, at least or exactly or at most 697, at least or exactly or at most 698, at least or exactly or at most 699, at least or exactly or at most 700, at least or exactly or at most 701, at least or exactly or at most 702, at least or exactly or at most 703, at least or exactly or at most 704, at least or exactly or at most 705, at least or exactly or at most 706, at least or exactly or at most 707, at least or exactly or at most 708, at least or exactly or at most 709, at least or exactly or at most 710, at least or exactly or at most 711, at least or exactly or at most 712, at least or exactly or at most 713, at least or exactly or at most 714, at least or exactly or at most 715, at least or exactly or at most 716, at least or exactly or at most 717, at least or exactly or at most 718, at least or exactly or at most 719, at least or exactly or at most 720, at least or exactly or at most 721, at least or exactly or at most 722, at least or exactly or at most 723, at least or exactly or at most 724, at least or exactly or at most 725, at least or exactly or at most 726, at least or exactly or at most 727, at least or exactly or at most 728, at least or exactly or at most 729, at least or exactly or at most 730, at least or exactly or at most 731, at least or exactly or at most 732, at least or exactly or at most 733, at least or exactly or at most 734, at least or exactly or at most 735, at least or exactly or at most 736, at least or exactly or at most 737, at least or exactly or at most 738, at least or exactly or at most 739, at least or exactly or at most 740, at least or exactly or at most 741, at least or exactly or at most 742, at least or exactly or at most 743, at least or exactly or at most 744, at least or exactly or at most 745, at least or exactly or at most 746, at least or exactly or at most 747, at least or exactly or at most 748, at least or exactly or at most 749, at least or exactly or at most 750, at least or exactly or at most 751, at least or exactly or at most 752, at least or exactly or at most 753, at least or exactly or at most 754, at least or exactly or at most 755, at least or exactly or at most 756, at least or exactly or at most 757, at least or exactly or at most 758, at least or exactly or at most 759, at least or exactly or at most 760, at least or exactly or at most 761, at least or exactly or at most 762, at least or exactly or at most 763, at least or exactly or at most 764, at least or exactly or at most 765, at least or exactly or at most 766, at least or exactly or at most 767, at least or exactly or at most 768, at least or exactly or at most 769, at least or exactly or at most 770, at least or exactly or at most 771, at least or exactly or at most 772, at least or exactly or at most 773, at least or exactly or at most 774, at least or exactly or at most 775, at least or exactly or at most 776, at least or exactly or at most 777, at least or exactly or at most 778, at least or exactly or at most 779, at least or exactly or at most 780, at least or exactly or at most 781, at least or exactly or at most 782, at least or exactly or at most 783, at least or exactly or at most 784, at least or exactly or at most 785, at least or exactly or at most 786, at least or exactly or at most 787, at least or exactly or at most 788, at least or exactly or at most 789, at least or exactly or at most 790, at least or exactly or at most 791, at least or exactly or at most 792, at least or exactly or at most 793, at least or exactly or at most 794, at least or exactly or at most 795, at least or exactly or at most 796, at least or exactly or at most 797, at least or exactly or at most 798, at least or exactly or at most 799, at least or exactly or at most 800, at least or exactly or at most 801, at least or exactly or at most 802, at least or exactly or at most 803, at least or exactly or at most 804, at least or exactly or at most 805, at least or exactly or at most 806, at least or exactly or at most 807, at least or exactly or at most 808, at least or exactly or at most 809, at least or exactly or at most 810, at least or exactly or at most 811, at least or exactly or at most 812, at least or exactly or at most 813, at least or exactly or at most 814, at least or exactly or at most 815, at least or exactly or at most 816, at least or exactly or at most 817, at least or exactly or at most 818, at least or exactly or at most 819, at least or exactly or at most 820, at least or exactly or at most 821, at least or exactly or at most 822, at least or exactly or at most 823, at least or exactly or at most 824, at least or exactly or at most 825, at least or exactly or at most 826, at least or exactly or at most 827, at least or exactly or at most 828, at least or exactly or at most 829, at least or exactly or at most 830, at least or exactly or at most 831, at least or exactly or at most 832, at least or exactly or at most 833, at least or exactly or at most 834, at least or exactly or at most 835, at least or exactly or at most 836, at least or exactly or at most 837, at least or exactly or at most 838, at least or exactly or at most 839, at least or exactly or at most 840, at least or exactly or at most 841, at least or exactly or at most 842, at least or exactly or at most 843, at least or exactly or at most 844, at least or exactly or at most 845, at least or exactly or at most 846, at least or exactly or at most 847, at least or exactly or at most 848, at least or exactly or at most 849, at least or exactly or at most 850, at least or exactly or at most 851, at least or exactly or at most 852, at least or exactly or at most 853, at least or exactly or at most 854, at least or exactly or at most 855, at least or exactly or at most 856, at least or exactly or at most 857, at least or exactly or at most 858, at least or exactly or at most 859, at least or exactly or at most 860, at least or exactly or at most 861, at least or exactly or at most 862, at least or exactly or at most 863, at least or exactly or at most 864, at least or exactly or at most 865, at least or exactly or at most 866, at least or exactly or at most 867, at least or exactly or at most 868, at least or exactly or at most 869, at least or exactly or at most 870, at least or exactly or at most 871, at least or exactly or at most 872, at least or exactly or at most 873, at least or exactly or at most 874, at least or exactly or at most 875, at least or exactly or at most 876, at least or exactly or at most 877, at least or exactly or at most 878, at least or exactly or at most 879, at least or exactly or at most 880, at least or exactly or at most 881, at least or exactly or at most 882, at least or exactly or at most 883, at least or exactly or at most 884, at least or exactly or at most 885, at least or exactly or at most 886, at least or exactly or at most 887, at least or exactly or at most 888, at least or exactly or at most 889, at least or exactly or at most 890, at least or exactly or at most 891, at least or exactly or at most 892, at least or exactly or at most 893, at least or exactly or at most 894, at least or exactly or at most 895, at least or exactly or at most 896, at least or exactly or at most 897, at least or exactly or at most 898, at least or exactly or at most 899, at least or exactly or at most 900, at least or exactly or at most 901, at least or exactly or at most 902, at least or exactly or at most 903, at least or exactly or at most 904, at least or exactly or at most 905, at least or exactly or at most 906, at least or exactly or at most 907, at least or exactly or at most 908, at least or exactly or at most 909, at least or exactly or at most 910, at least or exactly or at most 911, at least or exactly or at most 912, at least or exactly or at most 913, at least or exactly or at most 914, at least or exactly or at most 915, at least or exactly or at most 916, at least or exactly or at most 917, at least or exactly or at most 918, at least or exactly or at most 919, at least or exactly or at most 920, at least or exactly or at most 921, at least or exactly or at most 922, at least or exactly or at most 923, at least or exactly or at most 924, at least or exactly or at most 925, at least or exactly or at most 926, at least or exactly or at most 927, at least or exactly or at most 928, at least or exactly or at most 929, at least or exactly or at most 930, at least or exactly or at most 931, at least or exactly or at most 932, at least or exactly or at most 933, at least or exactly or at most 934, at least or exactly or at most 935, at least or exactly or at most 936, at least or exactly or at most 937, at least or exactly or at most 938, at least or exactly or at most 939, at least or exactly or at most 940, at least or exactly or at most 941, at least or exactly or at most 942, at least or exactly or at most 943, at least or exactly or at most 944, at least or exactly or at most 945, at least or exactly or at most 946, at least or exactly or at most 947, at least or exactly or at most 948, at least or exactly or at most 949, at least or exactly or at most 950, at least or exactly or at most 951, at least or exactly or at most 952, at least or exactly or at most 953, at least or exactly or at most 954, at least or exactly or at most 955, at least or exactly or at most 956, at least or exactly or at most 957, at least or exactly or at most 958, at least or exactly or at most 959, at least or exactly or at most 960, at least or exactly or at most 961, at least or exactly or at most 962, at least or exactly or at most 963, at least or exactly or at most 964, at least or exactly or at most 965, at least or exactly or at most 966, at least or exactly or at most 967, at least or exactly or at most 968, at least or exactly or at most 969, at least or exactly or at most 970, at least or exactly or at most 971, at least or exactly or at most 972, at least or exactly or at most 973, at least or exactly or at most 974, at least or exactly or at most 975, at least or exactly or at most 976, at least or exactly or at most 977, at least or exactly or at most 978, at least or exactly or at most 979, at least or exactly or at most 980, at least or exactly or at most 981, at least or exactly or at most 982, at least or exactly or at most 983, at least or exactly or at most 984, at least or exactly or at most 985, at least or exactly or at most 986, at least or exactly or at most 987, at least or exactly or at most 988, at least or exactly or at most 989, at least or exactly or at most 990, at least or exactly or at most 991, at least or exactly or at most 992, at least or exactly or at most 993, at least or exactly or at most 994, at least or exactly or at most 995, at least or exactly or at most 996, at least or exactly or at most 997, at least or exactly or at most 998, at least or exactly or at most 999, at least or exactly or at most 1000, at least or exactly or at most 1001, at least or exactly or at most 1002, at least or exactly or at most 1003, at least or exactly or at most 1004, at least or exactly or at most 1005, at least or exactly or at most 1006, at least or exactly or at most 1007, at least or exactly or at most 1008, at least or exactly or at most 1009, at least or exactly or at most 1010, at least or exactly or at most 1011, at least or exactly or at most 1012, at least or exactly or at most 1013, at least or exactly or at most 1014, at least or exactly or at most 1015, at least or exactly or at most 1016, at least or exactly or at most 1017, at least or exactly or at most 1018, at least or exactly or at most 1019, at least or exactly or at most 1020, at least or exactly or at most 1021, at least or exactly or at most 1022, at least or exactly or at most 1023, at least or exactly or at most 1024, at least or exactly or at most 1025, at least or exactly or at most 1026, at least or exactly or at most 1027, at least or exactly or at most 1028, at least or exactly or at most 1029, at least or exactly or at most 1030, at least or exactly or at most 1031, at least or exactly or at most 1032, at least or exactly or at most 1033, at least or exactly or at most 1034, at least or exactly or at most 1035, at least or exactly or at most 1036, at least or exactly or at most 1037, at least or exactly or at most 1038, at least or exactly or at most 1039, at least or exactly or at most 1040, at least or exactly or at most 1041, at least or exactly or at most 1042, at least or exactly or at most 1043, at least or exactly or at most 1044, at least or exactly or at most 1045, at least or exactly or at most 1046, at least or exactly or at most 1047, at least or exactly or at most 1048, at least or exactly or at most 1049, at least or exactly or at most 1050, at least or exactly or at most 1051, at least or exactly or at most 1052, at least or exactly or at most 1053, at least or exactly or at most 1054, at least or exactly or at most 1055, at least or exactly or at most 1056, at least or exactly or at most 1057, at least or exactly or at most 1058, at least or exactly or at most 1059, at least or exactly or at most 1060, at least or exactly or at most 1061, at least or exactly or at most 1062, at least or exactly or at most 1063, at least or exactly or at most 1064, at least or exactly or at most 1065, at least or exactly or at most 1066, at least or exactly or at most 1067, at least or exactly or at most 1068, at least or exactly or at most 1069, at least or exactly or at most 1070, at least or exactly or at most 1071, at least or exactly or at most 1072, at least or exactly or at most 1073, at least or exactly or at most 1074, at least or exactly or at most 1075, at least or exactly or at most 1076, at least or exactly or at most 1077, at least or exactly or at most 1078, at least or exactly or at most 1079, at least or exactly or at most 1080, at least or exactly or at most 1081, at least or exactly or at most 1082, at least or exactly or at most 1083, at least or exactly or at most 1084, at least or exactly or at most 1085, at least or exactly or at most 1086, at least or exactly or at most 1087, at least or exactly or at most 1088, at least or exactly or at most 1089, at least or exactly or at most 1090, at least or exactly or at most 1091, at least or exactly or at most 1092, at least or exactly or at most 1093, at least or exactly or at most 1094, at least or exactly or at most 1095, at least or exactly or at most 1096, at least or exactly or at most 1097, at least or exactly or at most 1098, at least or exactly or at most 1099, at least or exactly or at most 1100, at least or exactly or at most 1101, at least or exactly or at most 1102, at least or exactly or at most 1103, at least or exactly or at most 1104, at least or exactly or at most 1105, at least or exactly or at most 1106, at least or exactly or at most 1107, at least or exactly or at most 1108, at least or exactly or at most 1109, at least or exactly or at most 1110, at least or exactly or at most 1111, at least or exactly or at most 1112, at least or exactly or at most 1113, at least or exactly or at most 1114, at least or exactly or at most 1115, at least or exactly or at most 1116, at least or exactly or at most 1117, at least or exactly or at most 1118, at least or exactly or at most 1119, at least or exactly or at most 1120, at least or exactly or at most 1121, at least or exactly or at most 1122, at least or exactly or at most 1123, at least or exactly or at most 1124, at least or exactly or at most 1125, at least or exactly or at most 1126, at least or exactly or at most 1127, at least or exactly or at most 1128, at least or exactly or at most 1129, at least or exactly or at most 1130, at least or exactly or at most 1131, at least or exactly or at most 1132, at least or exactly or at most 1133, at least or exactly or at most 1134, at least or exactly or at most 1135, at least or exactly or at most 1136, at least or exactly or at most 1137, at least or exactly or at most 1138, at least or exactly or at most 1139, at least or exactly or at most 1140, at least or exactly or at most 1141, at least or exactly or at most 1142, at least or exactly or at most 1143, at least or exactly or at most 1144, at least or exactly or at most 1145, at least or exactly or at most 1146, at least or exactly or at most 1147, at least or exactly or at most 1148, at least or exactly or at most 1149, at least or exactly or at most 1150, at least or exactly or at most 1151, at least or exactly or at most 1152, at least or exactly or at most 1153, at least or exactly or at most 1154, at least or exactly or at most 1155, at least or exactly or at most 1156, at least or exactly or at most 1157, at least or exactly or at most 1158, at least or exactly or at most 1159, at least or exactly or at most 1160, at least or exactly or at most 1161, at least or exactly or at most 1162, at least or exactly or at most 1163, at least or exactly or at most 1164, at least or exactly or at most 1165, at least or exactly or at most 1166, at least or exactly or at most 1167, at least or exactly or at most 1168, at least or exactly or at most 1169, at least or exactly or at most 1170, at least or exactly or at most 1171, at least or exactly or at most 1172, at least or exactly or at most 1173, at least or exactly or at most 1174, at least or exactly or at most 1175, at least or exactly or at most 1176, at least or exactly or at most 1177, at least or exactly or at most 1178, at least or exactly or at most 1179, at least or exactly or at most 1180, at least or exactly or at most 1181, at least or exactly or at most 1182, at least or exactly or at most 1183, at least or exactly or at most 1184, at least or exactly or at most 1185, at least or exactly or at most 1186, at least or exactly or at most 1187, at least or exactly or at most 1188, at least or exactly or at most 1189, at least or exactly or at most 1190, at least or exactly or at most 1191, at least or exactly or at most 1192, at least or exactly or at most 1193, at least or exactly or at most 1194, at least or exactly or at most 1195, at least or exactly or at most 1196, at least or exactly or at most 1197, at least or exactly or at most 1198, at least or exactly or at most 1199, at least or exactly or at most 1200, at least or exactly or at most 1201, at least or exactly or at most 1202, at least or exactly or at most 1203, at least or exactly or at most 1204, at least or exactly or at most 1205, at least or exactly or at most 1206, at least or exactly or at most 1207, at least or exactly or at most 1208, at least or exactly or at most 1209, at least or exactly or at most 1210, at least or exactly or at most 1211, at least or exactly or at most 1212, at least or exactly or at most 1213, at least or exactly or at most 1214, at least or exactly or at most 1215, at least or exactly or at most 1216, at least or exactly or at most 1217, at least or exactly or at most 1218, at least or exactly or at most 1219, at least or exactly or at most 1220, at least or exactly or at most 1221, at least or exactly or at most 1222, at least or exactly or at most 1223, at least or exactly or at most 1224, at least or exactly or at most 1225, at least or exactly or at most 1226, at least or exactly or at most 1227, at least or exactly or at most 1228, at least or exactly or at most 1229, at least or exactly or at most 1230, at least or exactly or at most 1231, at least or exactly or at most 1232, at least or exactly or at most 1233, at least or exactly or at most 1234, at least or exactly or at most 1235, at least or exactly or at most 1236, at least or exactly or at most 1237, at least or exactly or at most 1238, at least or exactly or at most 1239, at least or exactly or at most 1240, at least or exactly or at most 1241, at least or exactly or at most 1242, at least or exactly or at most 1243, at least or exactly or at most 1244, at least or exactly or at most 1245, at least or exactly or at most 1246, at least or exactly or at most 1247, at least or exactly or at most 1248, at least or exactly or at most 1249, at least or exactly or at most 1250, at least or exactly or at most 1251, at least or exactly or at most 1252, at least or exactly or at most 1253, at least or exactly or at most 1254, at least or exactly or at most 1255, at least or exactly or at most 1256, at least or exactly or at most 1257, at least or exactly or at most 1258, at least or exactly or at most 1259, at least or exactly or at most 1260, at least or exactly or at most 1261, at least or exactly or at most 1262, at least or exactly or at most 1263, at least or exactly or at most 1264, at least or exactly or at most 1265, at least or exactly or at most 1266, at least or exactly or at most 1267, at least or exactly or at most 1268, at least or exactly or at most 1269, at least or exactly or at most 1270, at least or exactly or at most 1271, at least or exactly or at most 1272, at least or exactly or at most 1273, at least or exactly or at most 1274, at least or exactly or at most 1275, at least or exactly or at most 1276, at least or exactly or at most 1277, at least or exactly or at most 1278, at least or exactly or at most 1279, at least or exactly or at most 1280, at least or exactly or at most 1281, at least or exactly or at most 1282, at least or exactly or at most 1283, at least or exactly or at most 1284, at least or exactly or at most 1285, at least or exactly or at most 1286, at least or exactly or at most 1287, at least or exactly or at most 1288, at least or exactly or at most 1289, at least or exactly or at most 1290, at least or exactly or at most 1291, at least or exactly or at most 1292, at least or exactly or at most 1293, at least or exactly or at most 1294, at least or exactly or at most 1295, at least or exactly or at most 1296, at least or exactly or at most 1297, at least or exactly or at most 1298, at least or exactly or at most 1299, at least or exactly or at most 1300, at least or exactly or at most 1301, at least or exactly or at most 1302, at least or exactly or at most 1303, at least or exactly or at most 1304, at least or exactly or at most 1305, at least or exactly or at most 1306, at least or exactly or at most 1307, at least or exactly or at most 1308, at least or exactly or at most 1309, at least or exactly or at most 1310, at least or exactly or at most 1311, at least or exactly or at most 1312, at least or exactly or at most 1313, at least or exactly or at most 1314, at least or exactly or at most 1315, at least or exactly or at most 1316, at least or exactly or at most 1317, at least or exactly or at most 1318, at least or exactly or at most 1319, at least or exactly or at most 1320, at least or exactly or at most 1321, at least or exactly or at most 1322, at least or exactly or at most 1323, at least or exactly or at most 1324, at least or exactly or at most 1325, at least or exactly or at most 1326, at least or exactly or at most 1327, at least or exactly or at most 1328, at least or exactly or at most 1329, at least or exactly or at most 1330, at least or exactly or at most 1331, at least or exactly or at most 1332, at least or exactly or at most 1333, at least or exactly or at most 1334, at least or exactly or at most 1335, at least or exactly or at most 1336, at least or exactly or at most 1337, at least or exactly or at most 1338, at least or exactly or at most 1339, at least or exactly or at most 1340, at least or exactly or at most 1341, at least or exactly or at most 1342, at least or exactly or at most 1343, at least or exactly or at most 1344, at least or exactly or at most 1345, at least or exactly or at most 1346, at least or exactly or at most 1347, at least or exactly or at most 1348, at least or exactly or at most 1349, at least or exactly or at most 1350, at least or exactly or at most 1351, at least or exactly or at most 1352, at least or exactly or at most 1353, at least or exactly or at most 1354, at least or exactly or at most 1355, at least or exactly or at most 1356, at least or exactly or at most 1357, at least or exactly or at most 1358, at least or exactly or at most 1359, at least or exactly or at most 1360, at least or exactly or at most 1361, at least or exactly or at most 1362, at least or exactly or at most 1363, at least or exactly or at most 1364, at least or exactly or at most 1365, at least or exactly or at most 1366, at least or exactly or at most 1367, at least or exactly or at most 1368, at least or exactly or at most 1369, at least or exactly or at most 1370, at least or exactly or at most 1371, at least or exactly or at most 1372, at least or exactly or at most 1373, at least or exactly or at most 1374, at least or exactly or at most 1375, at least or exactly or at most 1376, at least or exactly or at most 1377, at least or exactly or at most 1378, at least or exactly or at most 1379, at least or exactly or at most 1380, at least or exactly or at most 1381, at least or exactly or at most 1382, at least or exactly or at most 1383, at least or exactly or at most 1384, at least or exactly or at most 1385, at least or exactly or at most 1386, at least or exactly or at most 1387, at least or exactly or at most 1388, at least or exactly or at most 1389, at least or exactly or at most 1390, at least or exactly or at most 1391, at least or exactly or at most 1392, at least or exactly or at most 1393, at least or exactly or at most 1394, at least or exactly or at most 1395, at least or exactly or at most 1396, at least or exactly or at most 1397, at least or exactly or at most 1398, at least or exactly or at most 1399, at least or exactly or at most 1400, at least or exactly or at most 1401, at least or exactly or at most 1402, at least or exactly or at most 1403, at least or exactly or at most 1404, at least or exactly or at most 1405, at least or exactly or at most 1406, at least or exactly or at most 1407, at least or exactly or at most 1408, at least or exactly or at most 1409, at least or exactly or at most 1410, at least or exactly or at most 1411, at least or exactly or at most 1412, at least or exactly or at most 1413, at least or exactly or at most 1414, at least or exactly or at most 1415, at least or exactly or at most 1416, at least or exactly or at most 1417, at least or exactly or at most 1418, at least or exactly or at most 1419, at least or exactly or at most 1420, at least or exactly or at most 1421, at least or exactly or at most 1422, at least or exactly or at most 1423, at least or exactly or at most 1424, at least or exactly or at most 1425, at least or exactly or at most 1426, at least or exactly or at most 1427, at least or exactly or at most 1428, at least or exactly or at most 1429, at least or exactly or at most 1430, at least or exactly or at most 1431, at least or exactly or at most 1432, at least or exactly or at most 1433, at least or exactly or at most 1434, at least or exactly or at most 1435, at least or exactly or at most 1436, at least or exactly or at most 1437, at least or exactly or at most 1438, at least or exactly or at most 1439, at least or exactly or at most 1440, at least or exactly or at most 1441, at least or exactly or at most 1442, at least or exactly or at most 1443, at least or exactly or at most 1444, at least or exactly or at most 1445, at least or exactly or at most 1446, at least or exactly or at most 1447, at least or exactly or at most 1448, at least or exactly or at most 1449, at least or exactly or at most 1450, at least or exactly or at most 1451, at least or exactly or at most 1452, at least or exactly or at most 1453, at least or exactly or at most 1454, at least or exactly or at most 1455, at least or exactly or at most 1456, at least or exactly or at most 1457, at least or exactly or at most 1458, at least or exactly or at most 1459, at least or exactly or at most 1460, at least or exactly or at most 1461, at least or exactly or at most 1462, at least or exactly or at most 1463, at least or exactly or at most 1464, at least or exactly or at most 1465, at least or exactly or at most 1466, at least or exactly or at most 1467, at least or exactly or at most 1468, at least or exactly or at most 1469, at least or exactly or at most 1470, at least or exactly or at most 1471, at least or exactly or at most 1472, at least or exactly or at most 1473, at least or exactly or at most 1474, at least or exactly or at most 1475, at least or exactly or at most 1476, at least or exactly or at most 1477, at least or exactly or at most 1478, at least or exactly or at most 1479, at least or exactly or at most 1480, at least or exactly or at most 1481, at least or exactly or at most 1482, at least or exactly or at most 1483, at least or exactly or at most 1484, at least or exactly or at most 1485, at least or exactly or at most 1486, at least or exactly or at most 1487, at least or exactly or at most 1488, at least or exactly or at most 1489, at least or exactly or at most 1490, at least or exactly or at most 1491, at least or exactly or at most 1492, at least or exactly or at most 1493, at least or exactly or at most 1494, at least or exactly or at most 1495, at least or exactly or at most 1496, at least or exactly or at most 1497, at least or exactly or at most 1498, at least or exactly or at most 1499, at least or exactly or at most 1500, at least or exactly or at most 1501, at least or exactly or at most 1502, at least or exactly or at most 1503, at least or exactly or at most 1504, at least or exactly or at most 1505, at least or exactly or at most 1506, at least or exactly or at most 1507, at least or exactly or at most 1508, at least or exactly or at most 1509, at least or exactly or at most 1510, at least or exactly or at most 1511, at least or exactly or at most 1512, at least or exactly or at most 1513, at least or exactly or at most 1514, at least or exactly or at most 1515, at least or exactly or at most 1516, at least or exactly or at most 1517, at least or exactly or at most 1518, at least or exactly or at most 1519, at least or exactly or at most 1520, at least or exactly or at most 1521, at least or exactly or at most 1522, at least or exactly or at most 1523, at least or exactly or at most 1524, at least or exactly or at most 1525, at least or exactly or at most 1526, at least or exactly or at most 1527, at least or exactly or at most 1528, at least or exactly or at most 1529, at least or exactly or at most 1530, at least or exactly or at most 1531, at least or exactly or at most 1532, at least or exactly or at most 1533, at least or exactly or at most 1534, at least or exactly or at most 1535, at least or exactly or at most 1536, at least or exactly or at most 1537, at least or exactly or at most 1538, at least or exactly or at most 1539, at least or exactly or at most 1540, at least or exactly or at most 1541, at least or exactly or at most 1542, at least or exactly or at most 1543, at least or exactly or at most 1544, at least or exactly or at most 1545, at least or exactly or at most 1546, at least or exactly or at most 1547, at least or exactly or at most 1548, at least or exactly or at most 1549, at least or exactly or at most 1550, at least or exactly or at most 1551, at least or exactly or at most 1552, at least or exactly or at most 1553, at least or exactly or at most 1554, at least or exactly or at most 1555, at least or exactly or at most 1556, at least or exactly or at most 1557, at least or exactly or at most 1558, and at least or exactly or at most 1559 consecutive nucleotides in the part of SEQ ID NO: 4 or 6 that encodes amino acids in the reading frame starting with residue 1.

The nucleic acid fragment of the invention discussed above typically has a sequence identity with the nucleotide sequence defined for i) or ii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The nucleic acid fragment of the invention discussed above may also have a sequence identity with the nucleotide sequence defined for iii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The nucleic acid fragment of the invention described above comprises in certain embodiments 1 or 2 distinct nucleic acid sequences each encoding a polypeptide of the invention, where each of said distinct nucleic acid sequences encodes at least or exactly or at most one immunogenic amino acid sequence present in or derived from SEQ ID NO: 1 or 2 and wherein said distinct nucleic acid sequences together encode immunogenic amino acid sequences present in or derived from one or both of SEQ ID NOs 1 and 2. In other words, such a nucleic acid fragment encodes several polypeptides of the invention. In some embodiments, the nucleic acid sequences are expressed as separate encoded proteins and in other embodiments as "pearls on a string", i.e. fused proteins.

It will be understood that the nucleic acid fragments of the invention may be used for production, carrier and vaccine purposes—the latter will require that the sequences are included in expression vectors that may lead to production of immunogenic proteins in the host animal receiving the vector.

The Vectors of the Invention

Vectors of the invention fall into several categories discussed infra. One preferred vector of the invention comprises in operable linkage and in the 5'-3' direction, an expression control region comprising an enhancer/promoter for driving expression of the nucleic acid fragment defined for option i) above, optionally a signal peptide coding sequence, a nucleotide sequence defined for option i), and optionally a terminator. Hence, such a vector constitutes an expression vector useful for effecting production in cells of the polypeptide of the invention. Since the polypeptides of the invention are bacterial of origin, recombinant production is conveniently effected in bacterial host cells, so here it is preferred that the expression control region drives expression in prokaryotic cell such as a bacterium, e.g. in E coli. However, if the vector is to drive expression in mammalian cell (as would be the case for a DNA vaccine vector), the expression control region should be adapted to this particular use.

At any rate, certain vectors of the invention are capable of autonomous replication.

Also, the vector of the invention may be one that is capable of being integrated into the genome of a host cell—this is particularly useful if the vector is use in the production of stably transformed cells, where the progeny will also include the genetic information introduced via the vector. Alternatively, vectors incapable of being integrated into the genome of a mammalian host cell are useful in e.g. DNA vaccination and other nucleic acid vaccination techniques.

Typically, the vector of the invention is selected from the group consisting of a virus, such as an attenuated virus (which may in itself be useful as a vaccine agent), a bacteriophage, a plasmid, a minichromosome, and a cosmid.

Particularly interesting vectors are viral vectors (in particular those useful as vaccine agents). These may be selected from the group consisting of a retrovirus vector, such as a lentivirus vector, an adenovirus vector, an adeno-associated virus vector, and a pox virus vector. Certain pox virus vectors are preferred, in particular vaccinia virus vectors. A particularly preferred vaccinia virus vector is a modified vaccinia Ankara (MVA) vector.

A more detailed discussion of vectors of the invention is provided in the following:

Polypeptides of the invention may be encoded by a nucleic acid molecule comprised in a vector. A nucleic acid sequence can be "heterologous," which means that it is in a context foreign to the cell in which the vector is being introduced, which includes a sequence homologous to a sequence in the cell but in a position within the host cell where it is ordinarily not found. Vectors include naked DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al, Molecular Cloning Laboratory Manual, $2^{nd}$ Edition, Cold Spring Harbor Laboratory Press, 1989; Ausuhel et al, Current Protocols in Molecular Biology, John Wiley, 1987-2002, both incorporated herein by reference). In addition to encoding the polypeptides of this invention, a vector of the present invention may encode polypeptide sequences such as a tag or immunogenicity enhancing peptide (e.g. an immunogenic carrier or a fusion partner that stimulates the immune system, such as a cytokine or active fragment thereof). Useful vectors encoding such fusion proteins include pIN vectors (Inouye S et al, Nucleic Acids Res. 1985 May 10; 13(9):3101-10), vectors encoding a stretch of histidines, and pGEX vectors, for use in generating glutathione S-transferase (GST) soluble fusion proteins for later purification and separation or cleavage.

Vectors of the invention may be used in a host cell to produce a polypeptide of the invention that may subsequently be purified for administration to a subject or the vector may be purified for direct administration to a subject for expression of the protein in the subject (as is the case when administering a nucleic acid vaccine).

Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural state. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference).

Naturally, it may be important to employ a promoter and/or enhancer that effectively direct(s) the expression of the DNA segment in the cell type or organism chosen for expression. Those of skill in the art of molecular biology generally know the use of promoters, enhancers, and cell type combinations for protein expression (see Sambrook et al, 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Examples of inducible elements, which are regions of a nucleic acid sequence that can be activated in response to a specific stimulus, include but are not limited to Immunoglobulin Heavy Chain, Immunoglobulin Light Chain, T Cell Receptor, HLA DQα and/or DQβ, β-Interferon, Interleukin-2, Interleukin-2 Receptor, MHC Class II 5, MHC Class II HLA-DRα, β-Actin, Muscle Creatine Kinase (MCK), Prealbumin (Transthyretin), Elastase I, Metallothionein (MTII), Collagenase, Albumin, α-Fetoprotein, γ-Globin, β—Globin, c-fos, c-HA-ras, Insulin, Neural Cell Adhesion Molecule (NCAM), a1-Antitrypain, H2B (TH2B) Histone, Mouse and/or Type I Collagen, Glucose-Regulated Proteins (GRP94 and GRP78), Rat Growth Hormone, Human Serum Amyloid A (SAA), Troponin I (TN I), Platelet-Derived Growth Factor (PDGF), Duchenne Muscular Dystrophy, SV40, Polyoma, Retroviruses, Papilloma Virus, Hepatitis B Virus, Human Immunodeficiency Virus, Cytomegalovirus (CMV) IE, and Gibbon Ape Leukemia Virus.

Inducible Elements include, but are not limited to MT II-Phorbol Ester (TFA)/Heavy metals; MMTV (mouse mammary tumor virus)—Glucocorticoids; β-Interferon—poly(rl)x/poly(rc); Adenovirus 5 E2—EIA; Collagenase-Phorbol Ester (TPA); Stromelysin-Phorbol Ester (TPA); SV40-Phorbol Ester (TPA); Murine MX Gene—Interferon, Newcastle Disease Virus; GRP78 Gene—A23187; α-2-Macroglobulin—IL-6; Vimentin—Serum; MHC Class I Gene H-2κb—Interferon; HSP70—E1A/SV40 Large T Antigen; Proliferin-Phorbol Ester/TPA; Tumor Necrosis Factor—PMA; and Thyroid Stimulating Hormonea Gene—Thyroid Hormone.

Also contemplated as useful in the present invention are the dectin-1 and dectin-2 promoters. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In various embodiments, the human cytomegalovirus (CMV) immediate early gene promoter, the SV40 early promoter, and the Rous sarcoma virus long terminal repeat can be used to obtain high level expression of a related polynucleotide to this invention. The use of other viral or mammalian cellular or bacterial phage promoters, which are well known in the art, to achieve expression of polynucleotides is contemplated as well.

In embodiments in which a vector is administered to a subject for expression of the protein, it is contemplated that a desirable promoter for use with the vector is one that is not down-regulated by cytokines or one that is strong enough that even if down-regulated, it produces an effective amount of the protein/polypeptide of the current invention in a subject to elicit an immune response. Non-limiting examples of these are CMV IE and RSV LTR. In other embodiments, a promoter that is up-regulated in the presence of cytokines is employed. The MHC I promoter increases expression in the presence of IFN-γ.

Tissue specific promoters can be used, particularly if expression is in cells in which expression of an antigen is desirable, such as dendritic cells or macrophages. The mammalian MHC I and MHC II promoters are examples of such tissue-specific promoters. 2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic and may be operable in bacteria or mammalian cells. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

2. Multiple Cloning Sites

Vectors can include a multiple cloning site (MCS), which is a nucleic acid region that contains multiple restriction enzyme sites, any of which can be used in conjunction with standard recombinant technology to digest the vector. Frequently, a vector is linearized or fragmented using a restriction enzyme that cuts within the MCS to enable exogenous sequences to be ligated to the vector. Techniques involving restriction enzymes and ligation reactions are well known to those of skill in the art of recombinant technology.

3. Splicing Sites

Most transcribed eukaryotic RNA molecules will undergo RNA splicing to remove introns from the primary transcripts. If relevant in the context of vectors of the present invention, vectors containing genomic eukaryotic sequences may require donor and/or acceptor splicing sites to ensure proper processing of the transcript for protein expression.

4. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

Terminators contemplated for use in the invention include any known terminator of transcription described herein or known to one of ordinary skill in the art, including but not limited to, for example, the bovine growth hormone terminator or viral termination sequences, such as the SV40 terminator. In certain embodiments, the termination signal may be a lack of transcribable or translatable sequence, such as due to a sequence truncation.

5. Polyadenylation Signals

In expression, particularly eukaryotic expression (as is relevant in nucleic acid vaccination), one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, markers that confer resistance to neomycin, puromycin, hygromycin, DHFR, GPT, zeocin or histidinol are useful selectable markers. In addition to markers conferring a phenotype that allows for the discrimination of transformants based on the implementation of conditions, other types of markers including screenable markers such as GFP for colorimetric analysis. Alternatively, screenable enzymes such as herpes simplex virus thymidine kinase (tk) or chloramphenicol acetyltransferase (CAT) may be utilized. One of skill in the art would also know how to employ immunologic markers that can be used in conjunction with FACS analysis. The marker used is not believed to be important, so long as it is capable of being expressed simultaneously with the nucleic acid encoding a protein of the invention. Further examples of selectable and screenable markers are well known to one of skill in the art.

The Transformed Cells of the Invention

Transformed cells of the invention are useful as organisms for producing the polypeptide of the invention, but also as simple "containers" of nucleic acids and vectors of the invention.

Certain transformed cells of the invention are capable of replicating the nucleic acid fragment defined for option i) of the second aspect of the invention. Preferred transformed cells of the invention are capable of expressing the nucleic acid fragment defined for option i).

For recombinant production it is convenient, but not a prerequisite that the transformed cell according is prokaryotic, such as a bacterium, but generally both prokaryotic and eukaryotic cells may be used.

suitable prokaryotic cells are bacterial cells selected from the group consisting of Escherichia (such as *E. coli.*), *Bacillus* [e.g. *Bacillus* subtilis], Salmonella, and Mycobacterium [preferably non-pathogenic, e.g. M. bovis BCG].

Eukaryotic cells can be in the form of yeasts (such as *Saccharomyces cerevisiae*) and protozoans. Alternatively, the transformed eukaryotic cells are derived from a multicellular organism such as a fungus, an insect cell, a plant cell, or a mammalian cell.

For production purposes, it is advantageous that the transformed cell of the invention is is stably transformed by having the nucleic acid defined above for option i) stably integrated into its genome, and in certain embodiments it is also preferred that the transformed cell secretes or carries on its surface the polypeptide of the invention, since this facilitates recovery of the polypeptides produced. A particular version of this embodiment is one where the transformed cell is a bacterium and secretion of the polypeptide of the invention is into the periplasmic space.

As noted above, stably transformed cells are preferred—these i.a. allows that cell lines comprised of transformed cells as defined herein may be established—such cell lines are particularly preferred aspects of the invention.

Further details on cells and cell lines are presented in the following:

Suitable cells for recombinant nucleic acid expression of the nucleic acid fragments of the present invention are prokaryotes and eukaryotes. Examples of prokaryotic cells include *E. coli*; members of the *Staphylococcus* genus, such as *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *Pseudomonas* genus such as Ps. *fluorescens*. Examples of eukaryotic cells include mammalian cells; insect cells; yeast cells such as members of the *Saccharomyces* genus (e.g. *S. cerevisiae*), members of the *Pichia* genus (e.g. *P. pastoris*), members of the *Hansenula* genus (e.g. *H. polymorpha*), members of the *Kluyveromyces* genus (e.g. *K. lactis* or *K. fragilis*) and members of the *Schizosaccharomyces* genus (e.g. *S. pombe*).

Techniques for recombinant gene production, introduction into a cell, and recombinant gene expression are well known in the art. Examples of such techniques are provided in references such as Ausubel, Current Protocols in Molecular Biology, John Wiley, 1987-2002, and Sambrook et al., Molecular Cloning, A Laboratory Manual, 2 nd Edition, Cold Spring Harbor Laboratory Press, 1989.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org) or from other depository institutions such as Deutsche Sammlung vor Micrroorganismen and Zellkulturen (DSM). An appropriate host can be determined by one of skill in the art based on the vector backbone and the desired result. A plasmid or cosmid, for example, can be introduced into a prokaryote host cell for replication of many vectors or expression of encoded proteins. Bacterial cells used as host cells for vector replication and/or expression include *Staphylococcus* strains, DH5a, JMI 09, and KC8, as well as a number of commercially available bacterial hosts such as SURE® Competent Cells and SOLOP ACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ Baculovirus expression system from CLONTECH®

In addition to the disclosed expression systems of the invention, other examples of expression systems include STRATAGENE® is COMPLETE CONTROL® Inducible Mammalian Expression System, which involves a synthetic ecdysone-inducible receptor, or its pET Expression System, an *E. coli*expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia*. One of skill in the art would know how to express a vector, such as an expression construct, to produce a nucleic acid sequence its cognate polypeptide, protein, or peptide.

Amplification of Nucleic Acids

Nucleic acids used as a template for amplification may be isolated from cells, tissues or other samples according to standard methodologies (Sambrook et al, Molecular Cloning, A Laboratory Manual, 2$^{nd}$ Edition, Cold Spring Harbor Laboratory Press, 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to sequences of genes identified herein are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals.

A number of template dependent processes are available to amplify the oligonucleotide sequences present in a given template sample. One of the best known amplification methods is the polymerase chain reaction (referred to as PCR(TM)) which is described in detail in U.S. Pat. Nos. 4,683,195, 4,683,202 and 4,800,159, and in Innis M.A. et al., Proc Natl Acad Sci USA 1988 December; 85(24):9436-9440, each of which is incorporated herein by reference in their entirety.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Methods of Gene Transfer

Suitable methods for nucleic acid delivery to effect expression of compositions of the present invention are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S.

U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (U.S. Pat. No. 5,789,215, incorporated herein by reference); by electroporation (U.S. Pat. No. 5,384,253, incorporated herein by reference); by calcium phosphate precipitation; by using DEAE dextran followed by polyethylene glycol (Gopal. T.V., Mol Cell Biol 1985 May; 5(5): 1188-90); by direct sonic loading; by liposome mediated transfection; by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (U.S. Patents 5,302, 523 and 5,464,765, each incorporated herein by reference); by *Agrobacterium* mediated transformation (U.S. Pat. Nos. 5,591,616 and 5,563,055, each incorporated herein by reference); or by PEG mediated transformation of protoplasts (U.S. Pat. Nos. 4,684,611 and 4,952,500, each incorporated herein by reference); by desiccation/inhibition mediated DNA uptake. Through the application of techniques such as these, organelle(s), cell(s), tissue(s) or organism(s) may be stably or transiently transformed.

The Antibodies of the Invention—and their Production/Isolation

Antibodies directed against the proteins of the invention are useful for affinity chromatography, immunoassays, and for distinguishing/identifying *staphylococcus* proteins as well as for passive immunisation and therapy.

Antibodies to the proteins of the invention, both polyclonal and monoclonal, may be prepared by conventional methods in general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of pg; injection is typically sufficient immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antiserum is obtained by bleeding the immunized animal into a glass or plastic container, incubating the blood at 25° C. for one hour, followed by incubating at 4° C. for 2-18 hours. The serum is recovered by centrifugation (eg. 1,000 g for 10 minutes). About 20-50 ml per bleed may be obtained from rabbits.

Monoclonal antibodies are prepared using the standard method of Kohler & Milstein [Nature (1975) 256: 495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective I aedium (elg. hypexanthine, aminopterin, thymidine medium, "HAT"). The resulting hybridomas are plated by limiting dilution, and are assayed for production of antibodies, which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly 32p and 1251), electron-dense reagents, enzymes, and ligands having specific binding partners. Enzymes are typically detected by their activity. For example, horseradish peroxidase is usually detected by its ability to convert 3,3', 5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, 1151 may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with, 1251, or with an anti-biotin MAb labeled with HRP. Other permutations and possibilities will be readily apparent to those of ordinary skill in the art, and are considered as equivalents within the scope of the instant invention.

According to the invention, the isolated monoclonal antibody or antibody analogue is preferably a monoclonal antibody selected from a multi-domain antibody such as a murine antibody, a chimeric antibody such as a humanized antibody, a fully human antibody, and single-domain antibody of a llama or a camel, or which is an antibody analogue selected from a fragment of an antibody such as an Fab or an $F(ab')_2$, an scFV; cf. also the definition of the term "antibody" presented above.

Compositions of the Invention; Vaccines

Pharmaceutical compositions, in particular vaccines, according to the invention may either be prophylactic (ie. to prevent infection) or therapeutic (ie, to treat disease after infection).

Such vaccines comprise immunising antigen(s), immunogen(s), polypeptide(s), protein(s) or nucleic acid(s), usually in combination with "pharmaceutically acceptable carriers", which include any carrier that does not itself induce the production of antibodies harmful to the individual receiving the composition.

In some embodiments of the invention, the pharmaceutical compositions such as vaccines include merely one single antigen, immunogen, polypeptide, protein, nucleic acid or vector of the invention, but in other embodiments, the pharmaceutical compositions comprise "cocktails" of the antigens or of the immunogens or of the polypeptides or of the protein or of the nucleic acids or of the vectors of the invention.

In particularly interesting embodiments, the pharmaceutical composition is an MVA vector mentioned herein, which encodes and can effect expression of at least 2 nucleic acid fragments of the invention.

Another interesting embodiment of a pharmaceutical composition comprises RNA as the active principle, i.e. at least one mRNA encoding a polypeptide of the invention.

An embodiment of a pharmaceutical composition of the invention comprises at least 2 distinct polypeptides of the invention described above, where each of said 2 distinct polypeptides comprises an immunogenic amino acid sequence present in or derived from SEQ ID NO: 1 or 2 and wherein said distinct polypeptides together comprise immunogenic amino acid sequences present in or derived from both SEQ ID NO: 1 and 2.

Another embodiment of the pharmaceutical composition of the invention comprises at least 2 distinct nucleic acid molecules (such as DNA and RNA) each encoding a polypeptide of the invention, where each of said distinct nucleic acid molecules encodes an immunogenic amino acid sequence present in or derived from any one of SEQ ID NOs: 1 or 2 and wherein said at distinct nucleic acid molecules together encode immunogenic amino acid sequences present in or derived from both SEQ ID NO 1 and 2.

Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles.

Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, H. pylori, etc. pathogen, cf. the description of immunogenic carriers supra.

The pharmaceutical compositions of the invention thus typically contain an immunological adjuvant, which is commonly an aluminium based adjuvant or one of the other adjuvants described in the following:

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi adjuvant system (RAS), (Ribi Immunochem, Hamilton, Mont.) containing 2% Squalene, 0.2% Tween 80, and one or more bacterial cell wall components from the group consisting of monophosphoryl lipid A (MPL), trehalose dimycolate (TDM), and cell wall skeleton (CWS), preferably MPL+CWS (Detox™); (3) saponin adjuvants such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor (TNF), etc.; and (6) other substances that act as immunostimulating agents to enhance the effectiveness of the composition. Alum and MF59™ adjuvants are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2"-2'-dipalmitoyl-sn-glycero-3-hydroxyphosphoryloxy)-ethylamine (MTP-PE), etc.

The immunogenic compositions (eg. the immunising antigen or immunogen or polypeptide or protein or nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunollogically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. nonhuma primate, primate, etc.), the capacity of the individual's immune system to synthesize antibodies or generally mount an immune response, the degree of protection desired, the formulation of the vaccine, the treating doctor's assessment of the medical situation, and other relevant factors. It is expected that the amount will fall in a relatively broad range that can be determined through routine trials. However, for the purposes of protein vaccination, the amount administered per immunization is typically in the range between 0.5 µg and 500 mg (however, often not higher than 5,000 µg), and very often in the range between 10 and 200 µg.

The immunogenic compositions are conventionally administered parenterally, eg, by injection, either subcutaneously, intramuscularly, or transdermally/transcutaneously. Additional formulations suitable for other modes of administration include oral and pulmonary formulations, suppositories, and transdermal applications. In the case of nucleic acid vaccination, also the intravenous or intraarterial routes may be applicable.

Dosage treatment may be a single dose schedule or a multiple dose schedule. The vaccine may be administered in conjunction with other immunoregulatory agents.

As an alternative to protein-based vaccines, DNA vaccination (also termed nucleic acid vaccination or gene vaccination) may be used.

A further aspect of the invention is as mentioned above the recognition that combination vaccines can be provided, wherein 2 or more antigens disclosed herein are combined to enhance the immune response by the vaccinated animal, including to optimize initial immune response and duration of immunity. For the purposes of this aspect of the invention, multiple antigenic fragments derived from the same, longer protein can also be used, such as the use of a combination of different lengths of polypeptide sequence fragments from one protein.

Thus, embodiments of the invention relate to a composition (or the use as a vaccine thereof) comprising 2 distinct (i.e. non-identical) proteinaceous immunogens disclosed herein wherein the first of said immunogens has the amino acid sequence SEQ ID NO: 1 or a variant or fragment thereof disclosed herein, in combination with a non-identical variant or fragment disclosed herein of the polypeptide having the amino acid sequence SEQ ID NO: 1.

Alternatively, the two proteinaceous immunogens may be comprised in one single fusion protein. Also, compositions comprising nucleic acids encoding these two distinct proteinaceous immunogens (either as separate nucleic acids encoding one immunogen each or as one single nucleic acid encoding both immunogens or encoding the fusion immunogen) are part of the present invention.

Other embodiments of the invention relate to a composition (or the use as a vaccine thereof) comprising 2 distinct proteinaceaous immunogens disclosed herein wherein the first of said immunogens has the amino acid sequence SEQ ID NO: 2 or a variant or fragment thereof disclosed herein, in combination with a non-identical variant or fragment disclosed herein of the polypeptide having the amino acid sequence SEQ ID NO: 2. Also, compositions comprising nucleic acids encoding these two distinct proteinaceous immunogens (either as separate nucleic acids encoding one immunogen each or as one single nucleic acid encoding both immunogens or encoding the fusion immunogen) are part of the present invention.

Still other embodiments of the invention relate to a composition (or the use as a vaccine thereof) comprising 2 distinct proteinaceaous immunogens disclosed herein wherein the first of said immunogens has the amino acid sequence SEQ ID NO: 1 or a variant or fragment thereof disclosed herein, in combination with a proteinaceous immunogen that has the amino acid sequence SEQ ID NO: 2 or a variant or fragment thereof disclosed herein. Also, compositions comprising nucleic acids encoding these two distinct proteinaceous immunogens (either as separate nucleic acids encoding one immunogen each or as one single nucleic acid encoding both immunogens or encoding the fusion immunogen) are part of the present invention.

In addition to this, the present invention also relates to immunogenic compositions that include a (poly)peptide of the present invention derived from SEQ ID NO: 1 (i.e. being one of the fragments or sequence variants disclosed herein) or being identical to SEQ ID NO: 1 in combination with any one of the polypeptides disclosed as SEQ ID NOs: 1-19 in WO 2012/136653 or with any one of the fragments and variants of these polypeptides disclosed on pages 9-18 in WO 2012/136653. Further, the present invention relates to immunogenic compositions that include a (poly)peptide of the present invention derived from SEQ ID NO: 2 (i.e. being one of the fragments or sequence variants disclosed herein) or being identical to SEQ ID NO: 2 in combination with any one of the polypeptides disclosed as SEQ ID NOs: 1-19 in WO 2012/136653 or with any one of the fragments or variants of these polypeptides disclosed on pages 9-18 in WO 2012/136653. Also, the present invention relates to immunogenic compositions that include two (poly)peptides of the present invention derived from SEQ ID NO: 1 and 2, respectively (i.e. being one of the fragments or sequence variants disclosed herein) or each or both being identical to SEQ ID NO: 1 and 2, in combination with any one of the polypeptides disclosed as SEQ ID NOs: 1-19 in WO 2012/136653 or with any one of the fragments or variants of these polypeptides disclosed on pages 9-18 in WO 2012/136653.

Also, the present invention also relates to immunogenic compositions that include a (poly)peptide of the present invention derived from SEQ ID NO: 1 (i.e. being one of the fragments or sequence variants disclosed herein) or being identical to SEQ ID NO: 1 in combination with any one of the polypeptides disclosed as SEQ ID NOs: 1-16 and 49 in WO 2015/082536 or with any of the fragments and variants of these polypeptides disclosed on pages 10-25 in WO 215/082536. Further, the present invention relates to immunogenic compositions that include a (poly)peptide of the present invention derived from SEQ ID NO: 2 (i.e. being one of the fragments or sequence variants disclosed herein) or being identical to SEQ ID NO: 2 in combination with any one of the polypeptides disclosed as SEQ ID NOs: 1-16 and 49 in WO 2015/082536 or with any one of the fragments or variants of these polypeptides disclosed on pages 10-25 in WO 2015/082536. Also, the present invention relates to immunogenic compositions that include two (poly)peptides of the present invention derived from SEQ ID NO: 1 and 2, respectively (i.e. being one of the fragments or sequence variants disclosed herein) or each or both being identical to SEQ ID NOs: 1 and 2, in combination with any one of the polypeptides disclosed as SEQ ID NOs: 1-16 and 49 in WO 2015/082536 or with any one of the fragments or variants of these polypeptides disclosed on pages 10-25 in WO 2015/082536.

The present invention also relates to immunogenic compositions that include a nucleic acid that encodes and is capable of effecting expression of a (poly)peptide of the present invention derived from SEQ ID NO: 1 (i.e. the (poly)peptide being one of the fragments or sequence variants disclosed herein) or being identical to SEQ ID NO: 1, in combination with a nucleic acid encoding and being capable of effecting expression of 1) any one of the polypeptides disclosed as SEQ ID NOs: 1-19 in WO 2012/136653 or 2) any one of the fragments and variants of these polypeptides disclosed on pages 9-18 in WO 2012/136653. Further, the present invention relates to immunogenic compositions that include nucleic acid that encodes a (poly)peptide of the present invention derived from SEQ ID NO: 2 (i.e. the (poly)peptide being one of the fragments or sequence variants disclosed herein) or being identical to SEQ ID NO: 2, in combination with a nucleic acid encoding and being capable of effecting expression of 1) any one of the polypeptides disclosed as SEQ ID NOs: 1-19 in WO 2012/136653 or 2) any one of the fragments or variants of these polypeptides disclosed on pages 9-18 in WO 2012/136653. The present invention also relates to immunogenic compositions that include one or more nucleic acids that encodes and is capable of effecting expression of (poly)peptides of the present invention derived from (or identical with) SEQ ID NOs: 1 and 2 (i.e. full-length proteins, fragments or sequence variants disclosed herein) in combination with a nucleic acid encoding and being capable of effecting expression of 1) any one of the polypeptides disclosed as SEQ ID NOs: 1-19 in WO 2012/136653 or 2) any one of the fragments and variants of these polypeptides disclosed on pages 9-18 in WO 2012/136653. Such a nucleic acid is typically an expression vector, either DNA-based or RNA-based. It is also within the ambit of the present invention that the 2 nucleic acids may be fused and part of one single nucleic acid that is capable of expressing two different immunogens or one single immunogen which constitutes a fusion protein. Thus the "combination of nucleic acids" can be in the form of separate nucleic acids that each encode a (poly)peptide or it can be in the form of a single nucleic acid that includes coding sequences from both of the (poly)peptides.

The present invention also relates to immunogenic compositions that include a nucleic acid that encodes and is capable of effecting expression of a (poly)peptide of the present invention derived from SEQ ID NO: 1 (i.e. the (poly)peptide being one of the fragments or sequence variants disclosed herein) or being identical to SEQ ID NO: 1, in combination with a nucleic acid encoding and being capable of effecting expression of 1) any one of the polypeptides disclosed as SEQ ID NOs: 1-16 and 49 in WO 2015/082536 or 2) any one of the fragments and variants of these polypeptides disclosed on pages 10-25 in WO 215/082536. Further, the present invention relates to immunogenic compositions that include nucleic acid that encodes a (poly)peptide of the present invention derived from SEQ ID NO: 2 (i.e. the (poly)peptide being one of the fragments or sequence variants disclosed herein) or being identical to SEQ ID NO: 2, in combination with a nucleic acid encoding and being capable of effecting expression of 1) any one of the polypeptides disclosed as SEQ ID NOs: 1-16 and 49 in WO 2015/082536 or 2) any one of the fragments or variants of these polypeptides disclosed on pages 10-25 in WO 2015/082536. Such a nucleic acid is typically an expression vector, either DNA-based or RNA-based. It is also within the ambit of the present invention that the 2 nucleic acids may be fused and part of one single nucleic acid that is capable of expressing two different immunogens or one single immunogen which constitutes a fusion protein. Thus the "combination of nucleic acids" can be in the form of separate nucleic acids that each encode a (poly)peptide or it can be in the form of a single nucleic acid that includes coding sequences from both of the (poly)peptides.

WO 2012/136653 and WO 2015/082536 are for these reasons incorporated in their entirety by reference herein.

Treatment Methods of the Invention

The method of the sixth aspect of the invention generally relates to induction of immunity and as such also entails method that relate to treatment, prophylaxis and amelioration of disease.

When immunization methods entail that a polypeptide of the invention or a composition comprising such a polypeptide is administered the animal (e.g. the human) typically receives between 0.5 and 5,000 µg of the polypeptide of the invention per administration.

In preferred embodiments of the sixth aspect, the immunization scheme includes that the animal (e.g. the human) receives a priming administration and one or more booster administrations.

Preferred embodiments of the $6^{th}$ aspect of the invention comprise that the administration is for the purpose of inducing protective immunity against S. aureus. In this embodiment it is particularly preferred that the protective immunity is effective in reducing the risk of attracting infection with S. aureus or is effective in treating or ameliorating infection with S. aureus.

As mentioned herein, the preferred vaccines of the invention induce humoral immunity, so it is preferred that the administration is for the purpose of inducing antibodies specific for S. aureus and wherein said antibodies or B-lymphocytes producing said antibodies are subsequently recovered from the animal.

But, as also mentioned the method of the 6th aspect may also be useful in antibody production, so in other embodiments the administration is for the purpose of inducing antibodies specific for S. aureus and wherein B-lymphocytes producing said antibodies are subsequently recovered from the animal and used for preparation of monoclonal antibodies.

Pharmaceutical compositions can as mentioned above comprise polypeptides, antibodies, or nucleic acids of the invention, optionally in admixture with polypeptides, antibodies or nucleic acids that are disclosed in WO 2012/136635 and/or WO 2015/082536. The pharmaceutical compositions will comprise a therapeutically effective amount thereof.

The term "therapeutically effective amount" or "prophylactically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. Reference is however made to the ranges for dosages of immunologically effective amounts of polypeptides, cf. above.

However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N. J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles.

Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

As is apparent from the claims, the invention also relates to related embodiments to the treatment and prophylaxis disclosed herein: the invention also includes embodiments where the polypeptide of the invention is for use as a pharmaceutical, in particular for use as a pharmaceutical in the treatment, prophylaxis or amelioration of infection with S. aureus;

the nucleic acid fragment of the invention or the vector of the invention is for use as a pharmaceutical, in particular for use as a pharmaceutical in the treatment, prophylaxis or amelioration of infection with S. aureus;

the transformed cell of the invention is for use as a pharmaceutical, in particular for use as a pharmaceutical in the treatment, prophylaxis or amelioration of infection with *S. aureus*.

the antibody, antibody fragment or antibody analogue of the invention is for use as a pharmaceutical, in particular for use as a pharmaceutical in the treatment, prophylaxis or amelioration of infection with *S. aureus*.

EXAMPLE 1

Protective Effect of SAR1262-25-519 in a Murine Model of Peritonitis

The purpose of the experiment was to test the potentially protective effect of immunization with the SAR1262-25-519 (a protein consisting of the amino acid sequence SEQ ID NO: 2, residues 25-519) in an animal model of peritonitis.
Materials
NMRI mice, female (Taconic, Denmark)
Aluminum hydroxide (Alhydrogel 2.0%; Brenntag, cat. no. 21645-51-2)
Freund's incomplete adjuvant (Sigma, cat. no. F5506-10X10ML)
*Staphylococcus aureus* MRSA252, ST_36 batch #2
SAR1262-25-519 (recombinantly produced at University of Southern Denmark)
Preparation of Vaccine The protein was mixed with adjuvant as described below. Both aluminium hydroxide and Freund's incomplete adjuvant were used for the first immunization, whereas only aluminium hydroxide was used for the second and third rounds of immunization.

The first immunization: Protein was mixed with aluminum hydroxide, in a ratio of 100 µl Alhydrogel per 125 µg protein, and incubated with end-over-end rotation for 1 hour. The suspension was centrifuged at 200×g for 2 minutes and the supernatant removed, so that the remaining volume equaled 50% of the injection volume per mouse times the number of mice. Freund's incomplete adjuvant was added, in a ratio of 1:1 to the volume of protein and Alhydrogel, and the mixture was vortexed vigorously for 1 hour.

Subsequent immunizations: The mice were boosted at regular intervals, using the same amount of protein mixed with Alhydrogel, as described above. Physiological saline was added to the suspension in order to reach the desired injection volume, when necessary.

Blood Sampling

Blood samples were collected by tail vein puncture following a short exposure under a heat lamp. The blood is collected in eppendorf tubes containing 5 µl 0.5 M EDTA, and the sample mixed vigorously in order to mix the blood with the EDTA. The tubes are centrifuged at 1800×g for 10 minutes, and the plasma fraction transferred to a second tube and stored at −80° C.
Immunization 8 female NMRI mice were immunized with recombinant SAR1262-25-519—these mice were numbered 9-16 in the text below. 6 mice in a control group were immunized with adjuvant only. Each mouse was immunized subcutaneously (SC) or intraperitoneally (IP) three times at 2-4 week intervals. At all three immunizations in the test group 50 µg protein was injected into each mouse. For the first immunization the proteins were mixed with aluminum hydroxide (Al(OH)$_3$) and Freund's incomplete adjuvant, whereas only Al(OH)$_3$ was used for the subsequent immunizations. Blood samples were collected from each animal approximately 10 days after the last immunization for analysis of antibody titer.
Preparation of Bacterial Inoculum The bacteria used in the animal model of peritonitis were prepared in advance and frozen to −80° C. in aliquots:

Bacterial matter is streaked out on a blood agar plate and incubated at 37° C. over night.

A single colony of *S. aureus* is used for the inoculation of 30 ml of tryptic soy broth (TSB) media. The culture is incubated at 37° C., with continuos shaking, over night.

The following day, 1 litre of TSB media is inoculated with 10 ml of the overnight culture, and incubated at 37° C. and continuous shaking for 6 hours. The bacterial suspension is centrifuged at 3000×g for 10 minutes, and the pellet washed twice in 400 ml sterile phosphate buffered saline (PBS). After each wash the bacterial suspension is centrifuged at 3000×g for 10 minutes. The bacterial pellet is resuspended in 10-15 ml PBS, and glycerol is added to the final concentration is 16%. The suspension is thoroughly mixed, aliquoted into 1 ml aliquots and stored at −80° C.

In order to determine the number of CFU per ml in the freeze stock, aliquots are thawed on ice, and serially diluted in sterile saline. The dilutions are plated on TSB agar plates, and incubated at 37° C., over night. The number of CFU per ml is determined the following day. The procedure is carried out in duplicate, i.e. for two aliquots, to verify that the aliquots are homogenous.

Immediately prior to inoculation, the aliquots were thawed and diluted in sterile saline to the desired inoculum size, i.e. number of colony forming units (CFU) per inoculum volume.
Challenge Setup The mice were housed at the Biomedical Laboratory at the University of Southern Denmark. The animals were kept in an environment characterized by a 12 hours light-dark cycle and temperature and humidity control. They had access to food and water ad libitum. The experimental procedures were carried out in accordance with the guidelines of the Danish
National Animal Ethics Committee.

The experiments were performed in class 2 certified facilities at the Biomedical Laboratory. Each mouse was inoculated intraperitoneally with 7.0×109 CFU of *Staphylococcus aureus* MRSA252. Following inoculation the mice were assessed daily to register symptoms and development of disease over the course of the 7 day challenge. To ensure a consistent evaluation of all animals, each animal was scored individually following the scale for clinical symptoms given in the following table.

|  | Score |
| --- | --- |
| Normal behavior | 0 = no; 1 = yes |
| Normal appearance | 0 = no; 1 = yes |
| Eye condition | 0 = normal; 1 = mild irritation; 2 = one closed; 3 = both closed |
| Diarrhea | 0 = no; 1 = yes |
| Changes in fur | 0 = no; 1 = yes |
| Hunchback | 0 = no; 1 = yes |
| Activity | 0 = normal; 1 = low activity; 2 = no activity |

The challenge was a lethal challenge without humane endpoints, hence those animals that could not combat the lethal *S. aureus* infection died of the infection. No animals were euthanized.

Results—Survival

The survival of immunized mice was compared to the survival of mice in the control group, i.e. mice only receiving adjuvants. FIG. 1 shows the survival curve of the mice immunized with SAR1262-25-519. One mouse (#16) had to be euthanized prior to challenge, hence only 7 vaccinated mice were subjected to challenge infection.

Results—Clinical Symptoms

The results of the clinical scoring are given in the following table. The raw data of the survival within each group is also given here (see the last lines beneath the daily registration of clinical symptoms).

|  | Scores for Mouse # | | | | | | |
| --- | --- | --- | --- | --- | --- | --- | --- |
|  | 9 | 10 | 11 | 12 | 13 | 14 | 15 |
| Day 1 post infection | | | | | | | |
| Normal behavior | 0 | 0 | 0 | 0 | 0 | 0 | 0 |
| Normal appearance | 0 | 0 | 0 | 0 | 0 | 0 | 0 |
| Eye condition | 2 | 1 | 3 | 2 | 3 | 1 | 1 |
| Diarrhea | 1 | 1 | 0 | 0 | 0 | 1 | 0 |
| Changes in fur | 1 | 1 | 1 | 1 | 1 | 1 | 1 |
| Hunch back | 1 | 1 | 1 | 1 | 1 | 1 | 1 |
| Activity | 1 | 1 | 1 | 1 | 1 | 1 | 0 |
| Dead (morning) | 0 | 0 | 0 | 0 | 0 | 0 | 0 |
| Day 2 post infection | | | | | | | |
| Normal behavior | 0 | 1 | 0 | 0 | 0 | — | 1 |
| Normal appearance | 0 | 1 | 0 | 0 | 0 | — | 1 |
| Eye condition | 0 | 0 | 1 | 0 | 0 | — | 0 |
| Diarrhea | 0 | 0 | 0 | 1 | 0 | — | 0 |
| Changes in fur | 1 | 0 | 1 | 1 | 1 | — | 0 |
| Hunch back | 1 | 0 | 1 | 1 | 1 | — | 0 |
| Activity] | 0 | 0 | 1 | 1 | 1 | — | 0 |
| Dead (morning) | 0 | 0 | 0 | 0 | 0 | 1 | 0 |
| Day 3 post infection | | | | | | | |
| Normal behavior | 1 | 1 | 0 | 0 | 0 | — | 1 |
| Normal appearance | 1 | 1 | 0 | 0 | 0 | — | 1 |
| Eye condition | 0 | 0 | 0 | 1 | 0 | — | 0 |
| Diarrhea | 0 | 0 | 0 | 1 | 0 | — | 0 |
| Changes in fur | 0 | 0 | 1 | 1 | 1 | — | 0 |
| Hunch back | 0 | 0 | 1 | 1 | 1 | — | 0 |
| Activity | 0 | 0 | 0 | 1 | 0 | — | 0 |
| Dead (morning) | 0 | 0 | 0 | 0 | 0 | 1 | 0 |
| Day 4 post infection | | | | | | | |
| Normal behavior | 0 | 1 | 1 | 0 | 0 | — | 1 |
| Normal appearance | 0 | 1 | 1 | 0 | 0 | — | 1 |
| Eye condition | 0 | 0 | 0 | 0 | 0 | — | 0 |
| Diarrhea | 0 | 0 | 0 | 0 | 0 | — | 0 |
| Changes in fur | 1 | 0 | 0 | 1 | 1 | — | 0 |
| Hunch back | 1 | 0 | 0 | 1 | 1 | — | 0 |
| Activity | 0 | 0 | 0 | 0 | 0 | — | 0 |
| Dead (morning) | 0 | 0 | 0 | 0 | 0 | 1 | 0 |
| Day 5 post infection | | | | | | | |
| Normal behavior | 0 | 1 | 1 | 0 | 0 | — | 1 |
| Normal appearance | 0 | 1 | 1 | 0 | 0 | — | 1 |
| Eye condition | 0 | 0 | 0 | 0 | 0 | — | 0 |
| Diarrhea | 0 | 0 | 0 | 0 | 0 | — | 0 |
| Changes in fur | 1 | 0 | 0 | 1 | 1 | — | 0 |
| Hunch back | 1 | 0 | 0 | 1 | 1 | — | 0 |
| Activity | 0 | 0 | 0 | 0 | 0 | — | 0 |
| Dead (morning) | 0 | 0 | 0 | 0 | 0 | 1 | 0 |
| Day 6 post infection | | | | | | | |
| Normal behavior | 1 | 1 | 1 | 0 | 0 | — | 1 |
| Normal appearance | 1 | 1 | 1 | 0 | 0 | — | 1 |
| Eye condition | 0 | 0 | 0 | 0 | 0 | — | 0 |
| Diarrhea | 0 | 0 | 0 | 0 | 0 | — | 0 |
| Changes in fur | 0 | 0 | 0 | 1 | 1 | — | 0 |
| Hunch back | 0 | 0 | 0 | 1 | 1 | — | 0 |
| Activity | 0 | 0 | 0 | 0 | 0 | — | 0 |
| Dead (morning) | 0 | 0 | 0 | 0 | 0 | 1 | 0 |
| Day 7 past infection | | | | | | | |
| Normal behavior | 1 | 1 | 0 | 0 | 0 | — | 1 |
| Normal appearance | 1 | 1 | 0 | 0 | 0 | — | 1 |
| Eye condition | 0 | 0 | 0 | 0 | 0 | — | 0 |
| Diarrhea | 0 | 0 | 0 | 0 | 0 | — | 0 |
| Changes in fur | 0 | 0 | 1 | 1 | 1 | — | 0 |
| Hunch back | 0 | 0 | 1 | 1 | 1 | — | 0 |
| Activity | 0 | 0 | 0 | 0 | 0 | — | 0 |
| Dead (morning) | 0 | 0 | 0 | 0 | 0 | 1 | 0 |
| CFU, right kidney | | | | | | | |
| dilution $10^2$ CFU/ml | 0 | 4 | 3 | >300 | >300 | — | 0 |
| dilution $10^3$ CFU/ml | 0 | 0 | 0 | >300 | 43 | — | 0 |
| dilution $10^4$ CFU/ml | 0 | 0 | 0 | 260 | 3 | — | 0 |

Results—Antibody Titre

Prior to challenge onset blood was drawn from the mice. The plasma was used for subsequent analysis of antibody titer, using ELISA. Antibody titres are shown in FIG. 2.

Conclusion

The lethal challenge with MRSA252 showed that prior immunization with SAR1262-25-519 had a protective effect, resulting in survival of a significant number of immunized animals. Immunization elicited an antibody response, though some animals immunized with SAR1262-25-519 had a lower antibody titer to the antigen compared to the other animals in that group.

EXAMPLE 2

Protective Effect of SAR2635-1-199 in a Murine Model of Peritonitis

The purpose of the experiment was to test the potentially protective effect of immunization with SAR2635-1-199 (the protein with the amino acid sequence SEQ ID NO: 1) in an animal model of peritonitis.

Materials

NMRI mice, female (Taconic, Denmark)
GERED Adjuvant LQ (Eiotechnik GmbH, #3000)
*Staphylococcus aureus* MRSA252, ST_36 batch #1
SAR2635-1-199 (recombinantly produced at the University of Southern Denmark)

Immunization 8 female NMRI mice were immunized with recombinant SAR 2635-1-199 in combination with adjuvant. 8 mice in the control group received adjuvant only. Each mouse was immunized subcutaneously three times at 2-3 weeks intervals (50, 36, and 16 days prior to initiation of challenge infection). At all three immunizations 50 µg protein formulated with GERBU adjuvant was injected into each mouse.

The protein was mixed with GERBU adjuvant in a ratio of 100 µl GERBU to 50 µg protein. If necessary, sterile saline was added to the suspension in order to reach the desired injection volume per animal. Before injection the solution was gently mixed using a pipette Preparation of Bacterial Inoculum and Challenge Setup These procedures were carried out exactly as described in Example 1.

Results—Survival

The survival of protein-immunized mice was compared to the survival of mice in the control group, i.e. mice only immunized with adjuvant. FIG. 3 shows the survival curve of the mice immunized with SAR2635-1-199. As is apparent, the vaccinated mice exhibited a significantly increased survival.

Conclusion

The lethal challenge with MRSA252 showed that prior immunization with SAR2635-1-199 had a protective effect, resulting in survival of a significant number of immunized animals.

EXAMPLE 3

The Protective Effect Fo SAR2635-1-199 and SAR1262-25-519 in a Murine Model of Peritonitis The purpose of the experiment was to test the potentially protective effect of immunization with the SAR2635-1-199 and SA 12<2-25-519 in an animal model of peritonitis. Immunization with both antigens was proven to elicit protection against an otherwise lethal infection with *Staphylococcus aureus* MRSA252. The supplier of experimental animals was different than in Examples 1 and 2, so the normal inoculation dose of 6.5×109 CFU of *Staphylococcus aureus* MRSA252 was not lethal to 90% (LD90) of the animals. This influences the results presented here, as proteins that appear non-protective in an LD45 challenge might generate protection in a "traditional" LD90 challenge.

Materials

NMRI mice, female (Janvier, France)
Aluminum hydroxide (Alhydrogel 2.0%; Brenntag, cat. no. 21645-51-2)
Freund's incomplete adjuvant (Sigma, cat. no. F5506-10X10ML)
*Staphylococcus aureus* MRSA252, ST_36, batch #2
SAR2635-1-199 (recombinantly produced at the University of Southern Denmark)
SAR1262-25-519 (recombinantly produced at the University of Southern Denmark)

Immunizations

Vaccines were prepared as described in Example 1.

2 groups of 20 female NMRI mice were immunized with recombinant protein in combination with adjuvant. The groups were immunized with either SAR2635-1-199 (polypeptide consisting of the amino acid sequence SEQ ID NO: 1) and SAR1262-25-519 (polypeptide consisting of residues 25-519 of SEQ ID NO: 2), respectively. 20 mice in a control group received adjuvant only. Each mouse was immunized subcutaneously three times at approximately two week intervals (42, 28 and 14 days prior to initiation of challenge infection). At all three immunizations 25 µg protein was injected into each mouse. For the first immunization the proteins were mixed with aluminum hydroxide (Al(OH)$_3$) and Freund's incomplete adjuvant, whereas only Al(OH)$_3$ was used for the subsequent immunizations.

Temperature Transponders

Four days before inoculation, temperature transponders (BMDS, cat. no. IPTT-300) were inserted into each mouse. The mice were briefly anaesthetised by inhalation of isoflurane, and a temperature transponder inserted underneath the skin on the lower back or side of the mouse.

Using a compatible wireless scanner (BMDS Smart Probe; BMDS, cat. no. DAS-7007s) body temperature could be registered when placing the scanner close to the transponders underneath the skin of the mouse.

Preparation of Bacterial Inoculum and Challenge Setup

These procedures were carried out exactly as described in Example 1.

Results—Survival

The survival of immunized mice was compared to the survival of mice in the control group, i.e. mice immunized with adjuvants only. FIGS. 4 and 5 survival curves of the mice immunized with SAR2635-1-199 and SAR1262-25-519, respectively.

Results—Clinical Symptoms

The results of the clinical scoring are given in the following tables. The raw data of the survival within each group is also given here (see the last lines beneath the daily registration of clinical symptoms). The first 3 tables show clinical data for SAR2635-1-199, whereas the last 3 tables show data for SAR1262-25-599.

| Mouse # | R1 | R2 | R3 | R4 | S1 | S2 | S3 | R1 | R2 | R3 | R4 | S1 | S2 | S3 | R1 | R2 | R3 | R4 | S1 | S2 | S3 |
|---|---|---|---|---|---|---|---|---|---|---|---|---|---|---|---|---|---|---|---|---|---|
| Day 0 post infection | | | | | | | | | | | | | | | | | | | | | |
| Temperature (°C) | 36.2 | 37.0 | 36.8 | 36.8 | 37.3 | 36.9 | 37.1 | 37.0 | 36.6 | 37.6 | 37.3 | 38.4 | 38.1 | 38.1 | 38.0 | 38.1 | 38.7 | 38.4 | 38.6 | 38.0 | 39.3 |
| Weight (g) | 35.7 | 33.5 | 37.0 | 39.5 | 40.5 | 37.2 | 36.5 | 36.8 | 33.9 | 39.8 | 37.9 | 44.8 | 38.0 | | 40.5 | 37.5 | 33.0 | 37.0 | 37.3 | 37.7 | 32.0 |
| Day 1 post infection | | | | | | | | | | | | | | | | | | | | | |
| Temperature (°C) | 38.5 | 37.9 | 37.9 | 37.8 | 38.5 | 37.7 | 37.5 | 37.6 | 37.5 | 37.3 | 36.7 | 37.2 | 37.3 | | 37.9 | | 38 | 37.4 | 37.6 | 37.4 | 36.3 |
| Weight (g) | 32.6 | 31.5 | 34 | 37.6 | 38.6 | 35.3 | 35 | 34.2 | 32.9 | 37 | 36.3 | 42.8 | 35.3 | | 40 | 100 | 30 | 35 | 37.5 | 37.3 | 30.8 |
| Weight loss (%) | 9 | 6 | 8 | 5 | 5 | 5 | 4 | 7 | 3 | 7 | 4 | 4 | 7 | | 1 | | 9 | 5 | -1 | 1 | 4 |
| Eye condition | 1 | 0 | 0 | 0 | 0 | 1 | 0 | 0 | 0 | 0 | 0 | 1 | 0 | | 0 | | 0 | 0 | 0 | 0 | 1 |
| Diarrhea | 0 | 1 | 0 | 0 | 1 | 1 | 1 | 0 | 0 | 0 | 0 | 1 | 1 | | 0 | | 0 | 0 | 0 | 0 | 0 |
| Changes in fur | 1 | 1 | 1 | 1 | 1 | 1 | 1 | 0 | 0 | 0 | 1 | 1 | 1 | | 0 | | 0 | 0 | 0 | 0 | 1 |
| Hunch back | 1 | 1 | 1 | 0 | 1 | 1 | 1 | 0 | 0 | 0 | 0 | 1 | 1 | | 0 | | 0 | 0 | 0 | 0 | 1 |
| Activity | 1 | 0 | 0 | 0 | 1 | 1 | 1 | 0 | 0 | 0 | 0 | 1 | 1 | | 0 | | 0 | 0 | 0 | 0 | 1 |
| Dead (morning) | 0 | 0 | 0 | 0 | 0 | 0 | 0 | 0 | 0 | 0 | 0 | 0 | 0 | | 1 | | 0 | 0 | 0 | 0 | 0 |
| Temperature (evening, °C) | 37.9 | 38 | 37.3 | 37.5 | 38.5 | 37.5 | 37.4 | 37.9 | 37.8 | 37.1 | 36.5 | 37.4 | 37.5 | | 38.5 | | 38.5 | 37.2 | 37.8 | 37.2 | 38 |
| Dead (evening) | 0 | 0 | 0 | 0 | 0 | 0 | 0 | 0 | 0 | 0 | 0 | 0 | 0 | | 0 | 1 | 0 | 0 | 0 | 0 | 0 |
| Day 2 post infection | | | | | | | | | | | | | | | | | | | | | |
| Temperature (°C) | 36.8 | 37.8 | 37.1 | 37.9 | 36.6 | 37.2 | 37.9 | 37 | 37.6 | 37 | 36 | 37.5 | | | 37.9 | | 37.8 | 37.1 | 37.7 | 37.2 | 37.6 |
| Weight (g) | 32.3 | 32.5 | 34.5 | 38.4 | 36.5 | 34.2 | 34.3 | 34.4 | 33.1 | 36.7 | 34.6 | 40.4 | 33 | | 40 | 100 | 28.8 | 35 | 37 | 37 | 29.4 |
| Weight loss (%) | 10 | 3 | 7 | 3 | 10 | 8 | 6 | 7 | 2 | 8 | 9 | 10 | 13 | | 1 | | 13 | 5 | 1 | 2 | 8 |
| Eye condition | 0 | 0 | 0 | 0 | 0 | 0 | 0 | 0 | 0 | 0 | 0 | 0 | 0 | | 0 | | 0 | 0 | 0 | 0 | 0 |
| Diarrhea | 0 | 0 | 0 | 0 | 1 | 0 | 0 | 0 | 0 | 0 | 0 | 1 | 1 | | 0 | | 1 | 0 | 0 | 0 | 1 |
| Changes in fur | 0 | 0 | 0 | 0 | 0 | 0 | 0 | 0 | 0 | 0 | 1 | 1 | 1 | | 0 | | 1 | 0 | 0 | 0 | 1 |
| Hunch back | 0 | 0 | 0 | 0 | 1 | 0 | 0 | 0 | 0 | 0 | 1 | 1 | 0 | | 0 | | 1 | 0 | 0 | 0 | 1 |
| Activity | 0 | 0 | 0 | 0 | 1 | 0 | 1 | 0 | 0 | 0 | 0 | 0 | 0 | | 0 | | 1 | 1 | 0 | 0 | 1 |
| Dead (morning) | 0 | 0 | 0 | 0 | 0 | 0 | 0 | 0 | 0 | 0 | 0 | 0 | 0 | | 0 | 1 | 0 | 0 | 0 | 0 | 0 |
| Day 3 post infection | | | | | | | | | | | | | | | | | | | | | |
| Temperature (°C) | 37.3 | 37.5 | 37.2 | 37.1 | 37.4 | 36.8 | 38 | 37.6 | 38 | 36.8 | 36 | 37.3 | 36.8 | | 38.3 | | 37 | 37.6 | 38.2 | 37.3 | 37.9 |
| Weight (g) | 34 | 33.5 | 35.5 | 39.5 | 37 | 34.5 | 34.3 | 36.2 | 34 | 37.5 | 33 | 42 | 34 | | 41.2 | 100 | 29.3 | 34.5 | 38.6 | 38.2 | 30.8 |
| Weight loss (%) | 5 | 0 | 4 | 0 | 9 | 7 | 6 | 2 | — | 6 | 13 | 6 | 11 | | -2 | | 11 | 7 | -3 | -1 | 4 |
| Eye condition | 0 | 0 | 0 | 0 | 0 | 0 | 0 | 0 | 0 | 0 | 0 | 0 | 0 | | 0 | | 0 | 0 | 0 | 0 | 0 |
| Diarrhea | 0 | 0 | 0 | 0 | 0 | 0 | 0 | 0 | 0 | 0 | 1 | 1 | 0 | | 0 | | 1 | 0 | 0 | 0 | 1 |
| Changes in fur | 1 | 0 | 0 | 0 | 1 | 0 | 0 | 0 | 0 | 0 | 1 | 1 | 0 | | 0 | | 1 | 1 | 0 | 0 | 1 |
| Hunch back | 0 | 0 | 0 | 0 | 0 | 0 | 0 | 0 | 0 | 0 | 1 | 1 | 0 | | 0 | | 1 | 1 | 0 | 0 | 0 |
| Activity | 0 | 0 | 0 | 0 | 0 | 0 | 0 | 0 | 0 | 0 | 0 | 0 | 0 | | 0 | | 0 | 0 | 0 | 0 | 0 |
| Dead (morning) | 0 | 0 | 0 | 0 | 0 | 0 | 0 | 0 | 0 | 0 | 0 | 0 | 0 | | 0 | 1 | 0 | 0 | 0 | 0 | 0 |
| Day 6 post infection | | | | | | | | | | | | | | | | | | | | | |
| Temperature (°C) | 37.9 | 37 | 37.9 | 37.6 | 37.4 | 37.6 | 37.9 | 37.9 | 38.4 | 37.2 | 37.1 | 37.6 | 37.7 | | 38.2 | | 37 | 37.5 | 37.9 | 37.4 | 37.2 |
| Weight (g) | 30.8 | 31.8 | 36.6 | 38.9 | 35.5 | 34.2 | 32.5 | 37.4 | 34 | 37.5 | 31 | 40 | 35 | | 42 | 100 | 32 | 33.5 | 42 | 40 | 31.5 |
| Weight loss (%) | 14 | 5 | 1 | 2 | 12 | 8 | 11 | -2 | 0 | 6 | 18 | 11 | 8 | | -4 | | 3 | 9 | -13 | -6 | 2 |
| Eye condition | 0 | 0 | 0 | 0 | 0 | 0 | 0 | 0 | 0 | 0 | 0 | 0 | 0 | | 0 | | 0 | 0 | 0 | 0 | 0 |
| Diarrhea | 0 | 0 | 0 | 0 | 0 | 0 | 0 | 0 | 0 | 0 | 0 | 0 | 0 | | 0 | | 0 | 0 | 0 | 0 | 0 |
| Changes in fur | 1 | 0 | 0 | 1 | 1 | 0 | 1 | 1 | 0 | 0 | 1 | 1 | 0 | | 1 | | 0 | 0 | 0 | 0 | 0 |
| Hunch back | 1 | 0 | 0 | 0 | 0 | 0 | 0 | 0 | 0 | 0 | 1 | 0 | 0 | | 0 | | 0 | 0 | 0 | 0 | 0 |
| Activity | 0 | 0 | 0 | 0 | 0 | 0 | 0 | 0 | 0 | 0 | 0 | 0 | 0 | | 0 | | 0 | 0 | 0 | 0 | 0 |
| Dead (morning) | 0 | 0 | 0 | 0 | 0 | 0 | 0 | 0 | 0 | 0 | 0 | 0 | 0 | | 0 | 1 | 0 | 0 | 0 | 0 | 0 |

| Mouse # | R1 | R2 | R3 | R4 | S1 | S2 | S3 | R1 | R2 | R3 | R4 | S1 | S2 | S3 | R1 | R2 | R3 | R4 | S1 | S2 | S3 |
|---|---|---|---|---|---|---|---|---|---|---|---|---|---|---|---|---|---|---|---|---|---|
| Day 7 post infection | | | | | | | | | | | | | | | | | | | | | |
| Temperature (° C.) | 37.9 | 37.6 | 36.3 | 37.7 | 37.1 | 37.4 | | 37.6 | 37.6 | 37 | 31.8 | 37.3 | 36.8 | | 38.2 | | | 37.5 | 37.2 | 37.2 | 36.2 |
| Weight (g) | 31.7 | 32 | 36.8 | 39.3 | 35.5 | 34 | 32.4 | 38 | 35 | 37.5 | 16 | 39.8 | 34.4 | | 39.8 | | 32 | 33 | 40.8 | 40.3 | 33 |
| Weight loss (%) | 11 | 4 | 1 | 1 | 12 | 9 | 11 | −3 | −3 | 6 | 16 | 11 | 9 | | 2 | 100 | 3 | 11 | −9 | −7 | −3 |
| Eye condition | 0 | 0 | 0 | 0 | 0 | 0 | 0 | 0 | 0 | 0 | 0 | 0 | 0 | | 0 | | 0 | 0 | 0 | 0 | 0 |
| Diarrhea | 0 | 0 | 0 | 0 | 0 | 0 | 0 | 0 | 0 | 0 | 1 | 0 | 0 | | 0 | | 0 | 0 | 0 | 0 | 0 |
| Changes in fur | 1 | 0 | 0 | 0 | 1 | 0 | 1 | 0 | 0 | 0 | 1 | 0 | 0 | | 0 | | 0 | 0 | 0 | 0 | 0 |
| Hunch back | 0 | 0 | 0 | 0 | 0 | 0 | 0 | 0 | 0 | 0 | 1 | 0 | 0 | | 0 | | 0 | 0 | 0 | 0 | 0 |
| Activity | 0 | 0 | 0 | 0 | 0 | 0 | 0 | 0 | 0 | 0 | 0 | 0 | 0 | | 0 | | 0 | 0 | 0 | 0 | 0 |
| Dead (morning) | 0 | 0 | 0 | 0 | 0 | 0 | 0 | | | | | | | | | | | | | | |
| Day 0 post infection | | | | | | | | | | | | | | | | | | | | | |
| Temperature (° C.) | 36.1 | 37.7 | 36.8 | 37.0 | 38.3 | 38.1 | 38.0 | 36.5 | 37.1 | 37.5 | 38.8 | 37.8 | 38.6 | | | | | 38.1 | | | 37.5 |
| Weight (g) | 38.2 | 36.5 | 36.5 | 33.2 | 37.5 | 33.9 | 34.7 | 39.0 | 35.1 | 37.0 | 38.0 | 37.4 | 32.8 | | 44.0 | | 37.6 39.0 | 37.0 | 35.0 | 38.9 | 48.5 |
| Day 1 post infection | | | | | | | | | | | | | | | | | | | | | |
| Temperature (° C.) | 37.4 | 38.6 | 37.4 | 38.4 | 37.7 | 35.1 | 38 | 37.2 | 37.5 | 38.3 | 36.2 | 37.6 | 37.8 | | 42.5 | 38.1 | 36 | 25.2 | | 38.4 | 35.8 |
| Weight (g) | 37 | 34.8 | 36.3 | 31.5 | 35.9 | 32.7 | 32.8 | 38.4 | 34 | 35.5 | 37 | 35.4 | 31 | | | 40.6 | 37.4 | | 34 | 37.8 | 47 |
| Weight loss (%) | 3 | 5 | 1 | 5 | 4 | 4 | 5 | 2 | 3 | 4 | 3 | 5 | 5 | | 3 | 4 | 4 | | 3 | 3 | 3 |
| Eye condition | 1 | 0 | 0 | 0 | 0 | 2 | 1 | 0 | 2 | 1 | 0 | 0 | 0 | | 1 | 0 | 1 | | 1 | 1 | 1 |
| Diarrhea | 1 | 1 | 1 | 1 | 1 | 1 | 1 | 1 | 1 | 1 | 1 | 1 | 1 | | 1 | 1 | 1 | | 1 | 1 | 1 |
| Changes in fur | 1 | 0 | 0 | 0 | 0 | 1 | 1 | 1 | 1 | 1 | 1 | 1 | 0 | | 1 | 1 | 1 | | 1 | 1 | 0 |
| Hunch back | 1 | 0 | 1 | 1 | 0 | 1 | 0 | 0 | 1 | 1 | 0 | 0 | 0 | | 1 | 0 | 1 | | 1 | 1 | 1 |
| Activity | 1 | 0 | 0 | 0 | 0 | 1 | 0 | 0 | 1 | 0 | 0 | 1 | 0 | | 1 | 1 | 1 | | 1 | 1 | 1 |
| Dead (morning) | 0 | 0 | 0 | 0 | 0 | 0 | 0 | 0 | 0 | 0 | 0 | 0 | 0 | | 0 | 0 | 0 | | 0 | 0 | 0 |
| Temperature (evening, ° C.) | 38.7 | 38.2 | 37.6 | 38.4 | 37.4 | 37.2 | 37.9 | 36.5 | 38 | 37.6 | 37.7 | 37.5 | 38.2 | | | 37.3 | 37.9 | 1 | | 38 | 38.5 |
| Dead (evening) | 0 | 0 | 0 | 0 | 0 | 0 | 0 | 0 | 0 | 0 | 0 | 0 | 0 | | 0 | 0 | 0 | | 0 | 0 | 0 |
| Day 2 post infection | | | | | | | | | | | | | | | | | | | | | |
| Temperature (° C.) | | 37.4 | 36.6 | 37.6 | 37 | 37.6 | 37.5 | 37.3 | 37.5 | 37.3 | 37.2 | 38 | 37.6 | | 38.4 | 37 | 36.8 | | 31.6 | 37.4 | 36.7 |
| Weight (g) | | 33 | 35 | 31.3 | 35.2 | 30.5 | 31.7 | 36.7 | 32.5 | 34 | 37 | 36 | 31.2 | | | 39 | 35.1 | | 10 | 35.8 | 44 |
| Weight loss (%) | | 10 | 4 | 6 | 6 | 10 | 9 | 6 | 7 | 8 | 2 | 4 | 5 | | 13 | 8 | 10 | | 10 | 8 | 9 |
| Eye condition | | 0 | 0 | 0 | 0 | 0 | 0 | 0 | 0 | 0 | 0 | 0 | 0 | | 0 | 0 | 0 | | 0 | 0 | 1 |
| Diarrhea | | 0 | 0 | 0 | 0 | 0 | 0 | 0 | 0 | 0 | 0 | 0 | 0 | | 1 | 1 | 1 | | 1 | 1 | 1 |
| Changes in fur | | 1 | 1 | 1 | 1 | 1 | 1 | 1 | 1 | 1 | 1 | 1 | 1 | | 1 | 1 | 1 | | 1 | 1 | 1 |
| Hunch back | | 0 | 0 | 0 | 0 | 0 | 0 | 0 | 1 | 0 | 0 | 0 | 0 | | 1 | 0 | 1 | | 1 | 1 | 1 |
| Activity | | 0 | 0 | 0 | 0 | 0 | 0 | 0 | 1 | 0 | 0 | 0 | 0 | | 0 | 0 | 0 | | 0 | 0 | 0 |
| Dead (morning) | | 0 | 0 | 0 | 0 | 0 | 0 | 0 | 0 | 0 | 0 | 0 | 0 | | | | | 1 | | | |
| Day 3 post infection | | | | | | | | | | | | | | | | | | | | | |
| Temperature (° C.) | | 37.7 | 37.7 | 37.7 | 37.8 | 37.3 | 37.2 | 36.8 | 37.6 | 37.4 | 38.8 | 38.4 | 37.6 | | 39 | 37 | 36.2 | | 32.8 | 37.8 | 35.8 |
| Weight (g) | | 34.2 | 36.5 | 32 | 36 | 30.5 | 32.5 | 37 | 34 | 35.1 | −2 | 36 | 32.5 | | 39.1 | 34.5 | | 6 | 37 | 42.5 |
| Weight loss (%) | | 6 | 0 | 4 | 4 | 10 | 6 | 5 | 3 | 5 | | 4 | 1 | | 11 | 8 | 12 | | 6 | 5 | 12 |
| Eye condition | | 0 | 0 | 0 | 0 | 0 | 0 | 0 | 0 | 0 | 0 | 0 | 0 | | 0 | 0 | 0 | | 0 | 0 | 0 |
| Diarrhea | | 0 | 0 | 0 | 0 | 0 | 1 | 1 | 1 | 0 | 0 | 0 | 0 | | 1 | 1 | 1 | | 1 | 1 | 1 |
| Changes in fur | | 0 | 1 | 0 | 0 | 0 | 1 | 1 | 1 | 0 | 0 | 0 | 0 | | 1 | 1 | 1 | | 1 | 1 | 1 |
| Hunch back | | 0 | 1 | 0 | 0 | 0 | 0 | 1 | 1 | 0 | 0 | 0 | 0 | | 1 | 1 | 1 | | 1 | 1 | 1 |
| Activity | | 0 | 1 | 0 | 0 | 0 | 0 | 0 | 0 | 0 | 0 | 0 | 0 | | 0 | 0 | 0 | | 0 | 0 | 0 |
| Dead (morning) | 1 | 0 | 0 | 0 | 0 | 0 | 0 | | | | | | | | | | | | | | |

-continued

| Mouse # | R1 | R2 | R3 | R4 | S1 | S2 | S3 | R1 | R2 | R3 | R4 | S1 | S2 | S3 | R1 | R2 | R3 | R4 | S1 | S2 | S3 |
|---|---|---|---|---|---|---|---|---|---|---|---|---|---|---|---|---|---|---|---|---|---|
| Day 6 post infection | | | | | | | | | | | | | | | | | | | | | |
| Temperature (° C.) | 38.2 | 37.3 | 38 | 38.2 | 37.3 | 37.7 | 37.1 | 37.6 | 37.1 | 39.6 | 38.1 | 37.9 | | 37.4 | 38.7 | 37.8 | | | 34 | 38.4 | |
| Weight (g) | 33.8 | 36.2 | 32.8 | 35.5 | 31.3 | 31.2 | 38 | 35.5 | 35 | −4 | 34.4 | 33.4 | | 15 | 36 | 36.9 | | | 3 | 37 | |
| Weight loss (%) | 7 | 1 | 1 | 5 | 8 | 10 | 3 | −1 | 5 | 0 | 8 | −2 | 0 | 15 | 15 | 5 | 0 | 0 | 5 | 5 | 0 |
| Eye condition | 0 | 0 | 0 | 0 | 0 | 0 | 0 | 0 | 0 | 0 | 0 | 0 | 0 | 0 | 0 | 0 | 0 | 0 | 0 | 0 | 0 |
| Diarrhea | 0 | 0 | 0 | 0 | 0 | 0 | 1 | 0 | 0 | 0 | 0 | 0 | 0 | 1 | 1 | 1 | 0 | 0 | 0 | 1 | 0 |
| Changes in fur | 0 | 0 | 0 | 0 | 0 | 0 | 0 | 0 | 0 | 0 | 0 | 0 | 0 | 0 | 1 | 1 | 0 | 0 | 0 | 0 | 0 |
| Hunch back | 0 | 0 | 0 | 0 | 0 | 0 | 0 | 0 | 0 | 0 | 0 | 0 | 0 | 0 | 1 | 1 | 0 | 0 | 0 | 1 | 0 |
| Activity | 0 | 0 | 0 | 0 | 0 | 0 | 0 | 0 | 0 | 0 | 0 | 0 | 0 | 0 | 0 | 0 | 0 | 0 | 0 | 0 | 0 |
| Dead (morning) | 0 | 0 | 0 | 0 | 0 | 0 | 0 | 0 | 0 | 0 | 0 | 0 | 0 | 0 | 0 | 0 | 0 | 0 | 0 | 0 | 0 |
| Day 7 post infection | | | | | | | | | | | | | | | | | | | | | |
| Temperature (° C.) | 37.9 | 36.7 | 37.9 | 38.3 | 36.6 | 37.1 | 37.1 | 37.3 | 37.7 | 38.5 | 37.9 | 37.8 | | 37.5 | 37.2 | 37.4 | | | 35.6 | 38.2 | |
| Weight (g) | 33.4 | 36.4 | 32.3 | 34.8 | 31.9 | 31.1 | 37.4 | 36 | 35 | −1 | 35.4 | 33.6 | | 15% | 36.1 | 35 | | | −2% | 37.3 | |
| Weight loss (%) | 8% | 0% | 3% | 7% | 6% | 10% | 4% | −3% | 5% | 0 | 5% | −2% | 0 | 15% | 15% | 10% | 0 | 0 | 0 | 4% | 0 |
| Eye condition | 0 | 0 | 0 | 0 | 0 | 0 | 0 | 0 | 0 | 0 | 0 | 0 | 0 | 0 | 0 | 0 | 0 | 0 | 0 | 0 | 0 |
| Diarrhea | 0 | 0 | 0 | 0 | 0 | 0 | 0 | 0 | 0 | 0 | 0 | 0 | 0 | 1 | 1 | 1 | 0 | 0 | 0 | 0 | 0 |
| Changes in fur | 0 | 0 | 0 | 0 | 0 | 0 | 1 | 0 | 0 | 0 | 0 | 0 | 0 | 0 | 1 | 1 | 0 | 0 | 0 | 0 | 0 |
| Hunch back | 0 | 0 | 0 | 0 | 0 | 0 | 1 | 0 | 0 | 0 | 0 | 0 | 0 | 0 | 0 | 0 | 0 | 0 | 0 | 0 | 0 |
| Activity | 0 | 0 | 0 | 0 | 0 | 0 | 0 | 0 | 0 | 0 | 0 | 0 | 0 | 0 | 0 | 0 | 0 | 0 | 0 | 0 | 0 |
| Dead (morning) | 0 | 0 | 0 | 0 | 0 | 0 | 0 | 0 | 0 | 0 | 0 | 0 | 0 | 0 | 0 | 0 | 0 | 0 | 0 | 0 | 0 |

Conclusion

The lethal challenge with MRSA252 showed that prior immunization with SAR2635-1-199 and SAR1262-25-519 had a protective effect, resulting in survival of a significant number of the immunized animals, even in an animal model, where the challenge dose of $6.5 \times 10^9$ CFU of *Staphylococcus aureus* MRSA252 only corresponds to LD45 (and not LD90).

Sequence Information

The sequence listing included sets forth the sequences of polypeptides and nucleic acids of the present invention. For easy reference, the sequences are presented in the following:

SEQ ID NO: 1
```
MTEKEKMLAEKWYDANFDQDLINERARAKDICFELNHTKPSDKNKRKELI
DELFQTTTDNVSISIPFDTDYGWNVKLGKNVYVNTNCYFMDGGQITIGDN
VFIGPNCGFYTATHPLNFHHRNEGFEKAGPINIGSNTWFGGHVAVLPGVT
IGEGSVIGAGSVVTKDIPPHSLAVGNPCKVVRKIDNEVPSEALNDETLN
```
(2',3'-cyclic-nucleotide 2'-phosphodiesterase/
Conserved virulence factor A); underlined part
used for recombinant expression (residues 25-519)

SEQ IN NO: 2
```
MNLLSLLLILLGIILGVVGGYVVARNLLLQKQSQARQTAEDIVNQAHKEA
DNIKKEKLLEAKEENQILREQTEAELRERRSELQRQETRLLQKEENLERK
SDLLDKKDEILEQKESKIEEKQQQVDAKESSVQTLIMKHEQELERISGLT
QEEAINEQLQRVEEELSQDIAVLVKEKEKEAKEKVDKTAKELLATAVQRL
AADHTSESTVSVVNLPNDEMKGRIIGREGRNIRTLETLTGIDLIIDDTPE
AVILSGFDPIRREIARTALVNLVSDGRIHPGRIEDMVEKARKEVDDIIRE
AGEQATFEVNAHNMHPDLVKIVGRLNYRTSYGQNVLKHSIEVANLASMLA
AELGEDETLAKRAGLLHDVGKAIDHEVEGSHVEIGVELAKKYGENETVIN
AIHSHHGDVEPTSIISILVAAADALSAARPGARKETLENYIRRLERLETL
SESYDGVEKAFAIQAGREIRVIVSPEEIDDLKSYRLARDIKNQIEDELQY
PGHIKVTVVRETRAVEYAK
```

(DNA encoding SEQ ID NO: 1)

SEQ ID NO: 3
```
ATGACTGAAAAAGAAAAATGTTAGCAGAAAAATGGTACGATGCAAACTT
TGATCAAGACTTAATCAATGAACGTGCACGAGCGAAAGATATTTGCTTTG
AATTAAATCATACAAAGCCGAGTGACAAAAATAAAGAAAGGAATTAATC
GATGAATTATTTCAAACAACAACAGACAATGTAAGTATTTCGATTCCTTT
TGATACAGATTATGGTTGGAACGTTAAACTAGGAAAAAATGTCTATGTAA
ACACCAATTGTTATTTTATGGATGGTGGACAGATTACAATTGGCGATAAT
GTTTTTATAGGACCTAATTGTGGATTCTACACAGCAACACATCCACTTAA
TTTTCATCATAGAAATGAAGGATTTGAAAAAGCAGGACCAATTAATATTG
GCAGTAATACTTGGTTTGGCGGACATGTAGCCGTGCTTCCGGGAGTGACG
ATTGGAGAAGGCAGTGTGATTGGTGCTGGTAGTGTTGTCACCAAAGATAT
TCCGCCACACAGTTTAGCGGTTGGAAACCCTTGTAAAGTCGTTCGTAAAA
TTGATAATGAGGTACCATCAGAAGCATTGAACGATGAAACACTAAATTAG
```

(DNA encoding SEQ ID NO: 2, underlined part
encoding residues 25-519 of SEQ ID NO: )

SEQ IN NO: 4
```
ATGAATTTATTAAGCCTCCTACTCATTTTGCTGGGGATCATTCTAGGAGT
TGTTGGAGGGTATGTTGTTGCCCGAAATTTGTTGCTTCAAAAGCAATCAC
AAGCTAGACAAACTGCCGAAGATATTGTAAATCAAGCACATAAAGAAGCT
GACAATATCAAAAAAGAGAAATTACTTGAGGCAAAAGAAGAAAACCAAAT
CCTAAGAGAACAAACTGAAGCAGAACTACGAGAAAGACGTAGCGAACTTC
AAAGACAAGAAACCCGACTTCTTCAAAAAGAAGAAAACTTAGAGCGTAAA
TCTGATCTATTAGATAAAAAGATGAGATTTTAGAGCAAAAAGAATCAAA
AATTGAAGAAAAACAACAACAAGTAGATGCAAAAGAGAGTAGTGTTCAAA
CGTTAATAATGAAGCATGAACAAGAATTAGAACGCATCTCCGGTCTCACT
CAAGAAGAAGCTATTAATGAGCAACTTCAAAGAGTAGAGGAAGAACTGTC
ACAAGATATTGCAGTACTTGTTAAAGAAAAAGAAAAAGAAGCTAAAGAAA
AAGTTGATAAAACAGCAAAAGAATTATTAGCTACAGCAGTACAAAGATTA
GCAGCAGATCACACAAGTGAATCAACGGTATCAGTAGTTAACTTACCTAA
TGATGAGATGAAAGGTCGAATCATTGGACGTGAAGGACGAAACATCCGTA
CACTTGAAACTTTAACTGGCATTGATTTAATTATTGATGACACACCAGAA
GCAGTTATATTATCTGGTTTTGATCCAATAAGAAGAGAAATTGCTAGAAC
AGCACTTGTTAACTTAGTATCTGATGGACGTATTCATCCAGGTAGAATTG
AAGATATGGTCGAAAAAGCTAGAAAAGAAGTAGACGATATTATAAGAGAA
GCAGGTGAACAAGCTACATTTGAAGTGAACGCACATAATATGCATCCTGA
CTTAGTAAAAATTGTAGGGCGTTTAAACTATCGTACAAGTTACGGTCAAA
ATGTACTTAAACATTCAATTGAAGTTGCGCATCTTGCTAGTATGTTAGCT
GCTGAGCTAGGCGAAGATGAGACATTAGCGAAACGAGCTGGACTTTTACA
TGATGTTGGTAAAGCAATTGATCATGAAGTAGAAGGTAGTCATGTTGAAA
TCGGTGTAGAATTAGCGAAAAAATATGGTGAAAATGAAACAGTTATTAAT
GCAATCCATTCTCACCATGGTGATGTTGAACCTACATCTATTATATCTAT
CCTTGTTGCTGCTGCAGATGCATTGTCTGCGGCTCGTCCAGGTGCAAGAA
AAGAAACATTAGAGAATTATATTCGTCGATTAGAACGTTTAGAAACGTTA
TCAGAAAGTTATGATGGTGTAGAAAAAGCATTTGCGATTCAGGCAGGTAG
AGAAATCCGAGTGATTGTATCTCCTGAAGAAATTGATGATTTAAAATCTT
ATCGATTGGCTAGAGATATTAAAAATCAGATTGAAGATGAATTACAATAT
CCTGGTCATATCAAGGTGACAGTTGTTCGAGAGACTAGAGCAGTAGAATA
TGCGAAATAA
```

(RNA encoding SEQ ID NO: 1)

SEQ ID NO: 5
```
AUGACUGAAAAAGAAAAAUGUUAGCAGAAAAAUGGUACGAUGCAAACUU
UGAUCAAGACUUAAUCAAUGAACGUGCACGAGCGAAAGAUAUUUGCUUUG
AAUUAAAUCAUACAAAGCCGAGUGACAAAAAUAAAGAAAGGAAUUAAUC
GAUGAAUUAUUUCAAACAACAACAGACAAUGUAAGUAUUUCGAUUCCUUU
UGAUACAGAUUAUGGUUGGAACGUUAAACUAGGAAAAAAUGUCUAUGUAA
ACACCAAUUGUUAUUUUAUGGAUGGUGGACAGAUUACAAUUGGCGAUAAU
GUUUUUAUAGGACCUAAUUGUGGAUUCUACACAGCAACACAUCCACUUAA
UUUUCAUCAUAGAAAUGAAGGAUUUGAAAAAGCAGGACCAAUUAAUAUUG
```

-continued

GCAGUAAUACUUGGUUUGGCGGACAUGUAGCCGUGCUUCCGGGAGUGACG

AUUGGAGAAGGCAGUGUGAUUGGUGCUGGUAGUGUUGUCACCAAAGAUAU

UCCGCCACACAGUUUAGCGGUUGGAAACCCUUGUAAAGUCGUUCGUAAAA

UUGAUAAUGAGGUACCAUCAGAAGCAUUGAACGAUGAAACACUAAAUUAG (RNA encoding SEQ ID NO: 2, underlined part encoding residues 25-519 of SEQ ID NO: 2)

SEQ ID NO: 6

AUGAAUUUAUUAAGCCUCCUACUCAUUUUGCUGGGGAUCAUUCUAGGAGU

UGUUGGAGGGUAUGUUGUUGCCCGAAAUUUGUUGCUUCAAAAGCAAUCAC

AAGCUAGACAAACUGCCGAAGAUAUUGUAAAUCAAGCACAUAAAGAAGCU

GACAAUAUCAAAAAAGAGAAAUUACUUGAGGCAAAAGAAGAAAACCAAAU

CCUAAGAGAACAAACUGAAGCAGAACUACGAGAAAGACGUAGCGAACUUC

AAAGACAAGAAACCCGACUUCUUCAAAAAGAAGAAAACUUAGAGCGUAAA

UCUGAUCUAUUAGAUAAAAAAGAUGAGAUUUUAGAGCAAAAAGAAUCAAA

AAUUGAAGAAAAACAACAACAAGUAGAUGCAAAAGAGAGUAGUGUUCAAA

CGUUAAUAAUGAAGCAUGAACAAGAAUUAGAACGCAUCUCCGGUCUCACU

CAAGAAGAAGCUAUUAAUGAGCAACUUCAAAGAGUAGAGGAAGAACUGUC

ACAAGAUAUUGCAGUACUUGUUAAAGAAAAAGAAAAAGAAGCUAAAGAAA

AAGUUGAUAAAACAGCAAAAGAAUUAUUAGCUACAGCAGUACAAAGAUUA

GCAGCAGAUCACACAAGUGAAUCAACGGUAUCAGUAGUUAACUUACCUAA

UGAUGAGAUGAAAGGUCGAAUCAUUGGACGUGAAGGACGAAACAUCCGUA

CACUUGAAACUUUAACUGGCAUUGAUUUAAUUAUUGAUGACACACCAGAA

GCAGUUAUAUUAUCUGGUUUUGAUCCAAUAAGAAGAGAAAUUGCUAGAAC

AGCACUUGUUAACUUAGUAUCUGAUGGACGUAUUCAUCCAGGUAGAAUUG

AAGAUAUGGUCGAAAAAGCUAGAAAAGAAGUAGACGAUAUUAUAAGAGAA

GCAGGUGAACAAGCUACAUUUGAAGUGAACGCACAUAAUAUGCAUCCUGA

CUUAGUAAAAAUUGUAGGGCGUUUAAACUAUCGUACAAGUUACGGUCAAA

AUGUACUUAAACAUUCAAUUGAAGUUGCGCAUCUUGCUAGUAUGUUAGCU

GCUGAGCUAGGCGAAGAUGAGACAUUAGCGAAACGAGCUGGACUUUUACA

UGAUGUUGGUAAAGCAAUUGAUCAUGAAGUAGAAGGUAGUCAUGUUGAAA

UCGGUGUAGAAUUAGCGAAAAAAUAUGGUGAAAAUGAAACAGUUAUUAAU

GCAAUCCAUUCUCACCAUGGUGAUGUUGAACCUACAUCUAUUAUAUCUAU

CCUUGUUGCUGCUGCAGAUGCAUUGUCUGCGGCUCGUCCAGGUGCAAGAA

AAGAAACAUUAGAGAAUUAUAUUCGUCGAUUAGAACGUUUAGAAACGUUA

UCAGAAAGUUAUGAUGGUGUAGAAAAAGCAUUUGCGAUUCAGGCAGGUAG

AGAAAUCCGAGUGAUUGUAUCUCCUGAAGAAAUUGAUGAUUUAAAAUCUU

AUCGAUUGGCUAGAGAUAUUAAAAAUCAGAUUGAAGAUGAAUUACAAUAU

CCUGGUCAUAUCAAGGUGACAGUUGUUCGAGAGACUAGAGCAGUAGAAUA

UGCGAAAUAA

The polypeptides of the present invention are also designated as follows herein:

SEQ ID NO: 1: SAR2635 SEQ ID NO: 2: SAR1262

The invention claimed is:

1. A method for inducing adaptive immunity against *S. aureus* in an animal by administering at least once an immunogenically effective amount of
a polypeptide comprising
a) SEQ ID NO: 1 or
b) an amino acid sequence consisting of at least or exactly 35 contiguous amino acid residues from the amino acid sequence of a), or
c) an amino acid sequence having a sequence identity of at least 80% with the amino acid sequence of a), or
d) an amino acid sequence having a sequence identity of at least 80% with the amino acid sequence of b),
said polypeptide being antigenic in a mammal.

2. The method according to claim 1, wherein, the animal receives between 0.5 and 5,000 μg of the polypeptide per administration.

3. The method according to claim 1, wherein the animal receives a first priming administration comprising said polypeptide and one or more booster administrations comprising said polypeptide.

4. The method according to claim 1, wherein the animal is a human being.

5. The method according to claim 1, wherein the at least or exactly 35 contiguous amino acids are at least or exactly or at most 36 contiguous amino acids, at least or exactly or at most 37 contiguous amino acids, at least or exactly or at most 38 contiguous amino acids, at least or exactly or at most 39 contiguous amino acids, at least or exactly or at most 40 contiguous amino acids, at least or exactly or at most 41 contiguous amino acids, at least or exactly or at most 42 contiguous amino acids, at least or exactly or at most 43 contiguous amino acids, at least or exactly or at most 44 contiguous amino acids, at least or exactly or at most 45 contiguous amino acids, at least or exactly or at most 46 contiguous amino acids, at least or exactly or at most 47 contiguous amino acids, at least or exactly or at most 48 contiguous amino acids, at least or exactly or at most 49 contiguous amino acids, at least or exactly or at most 50 contiguous amino acids, at least or exactly or at most 51 contiguous amino acids, at least or exactly or at most 52 contiguous amino acids, at least or exactly or at most 53 contiguous amino acids, at least or exactly or at most 54 contiguous amino acids, at least or exactly or at most 55 contiguous amino acids, at least or exactly or at most 56 contiguous amino acids, at least or exactly or at most 57 contiguous amino acids, at least or exactly or at most 58 contiguous amino acids, at least or exactly or at most 59 contiguous amino acids, at least or exactly or at most 60 contiguous amino acids, at least or exactly or at most 61 contiguous amino acids, at least or exactly or at most 62 contiguous amino acids, at least or exactly or at most 63 contiguous amino acids, at least or exactly or at most 64 contiguous amino acids, at least or exactly or at most 65 contiguous amino acids, at least or exactly or at most 66 contiguous amino acids, at least or exactly or at most 67 contiguous amino acids, at least or exactly or at most 68 contiguous amino acids, at least or exactly or at most 69 contiguous amino acids, at least or exactly or at most 70 contiguous amino acids, at least or exactly or at most 71 contiguous amino acids, at least or exactly or at most 72 contiguous amino acids, at least or exactly or at most 73 contiguous amino acids, at least or exactly or at most 74 contiguous amino acids, at least or exactly or at most 75 contiguous amino acids, at least or exactly or at most 76 contiguous amino acids, at least or exactly or at most 77 contiguous amino acids, at least or exactly or at most 78 contiguous amino acids, at least or exactly or at most 79 contiguous amino acids, at least or exactly or at most 80 contiguous amino acids, at least or exactly or at most 81 contiguous amino acids, at least or exactly or at most 82 contiguous amino acids, at least or exactly or at most 83 contiguous amino acids, at least or exactly or at most 84 contiguous amino acids, at least or exactly or at most 85 contiguous amino acids, at least or exactly or at most 86 contiguous amino acids, at least or exactly or at most 87 contiguous amino acids, at least or exactly or at most 88 contiguous amino acids, at least or exactly or at most 89 contiguous amino acids, at least or exactly or at most 90 contiguous amino acids, at least or exactly or at most 91 contiguous amino acids, at least or exactly or at most 92 contiguous amino acids, at least or exactly or at most 93 contiguous amino acids, at least or exactly or at most 94 contiguous amino acids, at least or exactly or at most 95 contiguous amino acids, at least or exactly or at most 96 contiguous amino acids, at least or exactly or at most 97 contiguous amino acids, at least or exactly or at most 98, at least or exactly or at most 99 contiguous amino acids, at least or exactly or at most 100 contiguous amino acids, at least or exactly or at most 101 contiguous amino acids, at least or exactly or at most 102 contiguous amino acids, at least or exactly or at most 103, at least or exactly or at most 104 contiguous amino acids, at least or exactly or at most 105 contiguous amino acids, at least or exactly or at most 106 contiguous amino acids, at least or exactly or at most 107 contiguous amino acids, at least or exactly or at most 108 contiguous amino acids, at least or exactly or at most 109 contiguous amino acids, at least or exactly or at most 110 contiguous amino acids, at least or exactly or at most 111 contiguous amino acids, at least or exactly or at most 112 contiguous amino acids, at least or exactly or at most 113 contiguous amino acids, at least or exactly or at most 114 contiguous amino acids, at least or exactly or at most 115 contiguous amino acids, at least or exactly or at most 116 contiguous amino acids, at least or exactly or at most 117 contiguous amino acids, at least or exactly or at most 118 contiguous amino acids, at least or exactly or at most 119 contiguous amino acids, at least or exactly or at most 120 contiguous amino acids, at least or exactly or at most 121 contiguous amino acids, at least or exactly or at most 122 contiguous amino acids, at least or exactly or at most 123 contiguous amino acids, at least or exactly or at most 124 contiguous amino acids, at least or exactly or at most 125 contiguous amino acids, at least or exactly or at most 126 contiguous amino acids, at least or exactly or at most 127 contiguous amino acids, at least or exactly or at most 128 contiguous amino acids, at least or exactly or at most 129 contiguous amino acids, at least or exactly or at most 130 contiguous amino acids, at least or exactly or at most 131 contiguous amino acids, at least or exactly or at most 132 contiguous amino acids, at least or exactly or at most 133 contiguous amino acids, at least or exactly or at most 134 contiguous amino acids, at least or exactly or at most 135 contiguous amino acids, at least or exactly or at most 136 contiguous amino acids, at least or exactly or at most 137 contiguous amino acids, at least or exactly or at most 138 contiguous amino acids, at least or exactly or at most 139 contiguous amino acids, at least or exactly or at most 140 contiguous amino acids, at least or exactly or at most 141 contiguous amino acids, at least or exactly or at most 142 contiguous amino acids, at least or exactly or at most 143 contiguous amino acids, at least or exactly or at most 144 contiguous amino acids, at least or exactly or at most 145 contiguous amino acids, at least or exactly or at most 146 contiguous amino acids, at least or exactly or at most 147 contiguous amino acids, at least or exactly or at most 148 contiguous amino acids, at least or exactly or at most 149 contiguous amino acids, at least or exactly or at most 150 contiguous amino acids, at least or exactly or at most 151 contiguous amino acids, at least or exactly or at most 152 contiguous amino acids, at least or exactly or at most 153 contiguous amino acids, at least or exactly or at most 154 contiguous amino acids, at least or exactly or at most 155 contiguous amino acids, at least or exactly or at most 156 contiguous amino acids, at least or exactly or at most 157 contiguous amino acids, at least or exactly or at most 158 contiguous amino acids, at least or exactly or at most 159 contiguous amino acids, at least or exactly or at most 160 contiguous amino acids, at least or exactly or at most 161 contiguous amino acids, at least or exactly or at most 162 contiguous amino acids, at least or exactly or at most 163 contiguous amino acids, at least or exactly or at most 164 contiguous amino acids, at least or exactly or at most 165 contiguous amino acids, at least or exactly or at most 166 contiguous amino acids, at least or exactly or at most 167 contiguous amino acids, at least or exactly or at most 168 contiguous amino acids, at least or exactly or at most 169 contiguous amino acids, at least or exactly or at most 170 contiguous amino acids, at least or exactly or at most 171 contiguous amino acids, at least or exactly or at most 172 contiguous amino acids, at least or exactly or at most 173 contiguous amino acids, at least or exactly or at most 174 contiguous amino acids, at least or exactly or at most 175 contiguous amino acids, at least or exactly or at most 176 contiguous amino acids, at least or exactly or at most 177 contiguous amino acids, at least or exactly or at most 178 contiguous amino acids, at least or exactly or at most 179 contiguous amino acids, at least or exactly or at most 180 contiguous amino acids, at least or exactly or at most 181 contiguous amino acids, at least or exactly or at most 182 contiguous amino acids, at least or exactly or at most 183 contiguous amino acids, at least or exactly or at most 184 contiguous amino acids, at least or exactly or at most 185 contiguous amino acids, at least or exactly or at most 186 contiguous amino acids, at least or exactly or at most 187 contiguous amino acids, at least or exactly or at most 188 contiguous amino acids, at least or exactly or at most 189 contiguous amino acids, at least or exactly or at most 190 contiguous amino acids, at least or exactly or at most 191 contiguous amino acids, at least or exactly or at most 192 contiguous amino acids, at least or exactly or at most 193 contiguous amino acids, at least or exactly or at most 194 contiguous amino acids, at least or exactly or at most 195 contiguous amino acids, at least or exactly or at most 196 contiguous amino acids, at least or exactly or at most 197 contiguous amino acids, or at least or exactly or at most 198 contiguous amino acid residues of SEQ ID NO: 1.

6. The method according to claim 1, wherein the sequence identity with the amino acid sequence of a) or b) is at least 85%, at least 90%, at least 91%, at least 92%, at least 93%, at least 94%, at least 95%, at least 96%, at least 97%, at least 98%, and at least 99%.

7. The method according to claim 1, wherein the at least or exactly 35 contiguous amino acid residues has an N-terminal amino acid residue corresponding to any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40,42, 43, 44, 45, 46, 47, 48, 49, 50, 51, 52, 53, 54, 55, 56, 57, 58, 59, 60, 61, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, or 165 in SEQ ID NO: 1.

8. The method according to claim 1, wherein the polypeptide is fused or conjugated to an immunogenic carrier molecule.

9. The method according to claim 8, wherein the immunogenic carrier molecule is a polypeptide that induces T-helper lymphocyte responses in humans.

10. The method according to claim 1, wherein the polypeptide induces adaptive immunity in the form of a humoral and/or a cellular adaptive immune response.

11. A pharmaceutical composition comprising a polypeptide defined in claim 1 and a pharmaceutically acceptable carrier, vehicle or diluent, and an immunological adjuvant.

12. The pharmaceutical composition according to claim 11, wherein the immunological adjuvant is an aluminium based adjuvant.

13. The method of claim 9 wherein said immunogenic carrier molecule is an immunogenic carrier protein selected from the group consisting of keyhole limpet hemocyanin, tetanus toxoid, and diphtheria toxoid.

* * * * *